(12) United States Patent
Goutayer et al.

(10) Patent No.: US 11,938,204 B2
(45) Date of Patent: Mar. 26, 2024

(54) OIL-IN-WATER EMULSIONS OF WHICH THE OIL PHASE IS IN THE FORM OF A MIXTURE OF DROPS OF DIFFERENT SIZES

(71) Applicant: CAPSUM, Marseilles (FR)

(72) Inventors: Mathieu Goutayer, Saint Malo (FR); Yan Eric Pafumi, Gardanne (FR); Lucie Chatry, Chateauroux-les-Alpes (FR); Hélène Balbusquier, Sainte-Radegonde (FR)

(73) Assignee: CAPSUM, Marseilles (FR)

(*) Notice: Subject to any disclaimer, the term of this patent is extended or adjusted under 35 U.S.C. 154(b) by 257 days.

(21) Appl. No.: 16/077,049

(22) PCT Filed: Feb. 10, 2017

(86) PCT No.: PCT/EP2017/053063
§ 371 (c)(1),
(2) Date: Aug. 10, 2018

(87) PCT Pub. No.: WO2017/137597
PCT Pub. Date: Aug. 17, 2017

(65) Prior Publication Data
US 2021/0121375 A1    Apr. 29, 2021

(30) Foreign Application Priority Data
Feb. 12, 2016 (FR) ...................................... 1651172

(51) Int. Cl.
| | | |
|---|---|---|
| *A61K 8/06* | (2006.01) | |
| *A61K 8/11* | (2006.01) | |
| *A61K 8/25* | (2006.01) | |
| *A61K 8/73* | (2006.01) | |
| *A61K 8/81* | (2006.01) | |
| *A61K 8/898* | (2006.01) | |
| *A61K 8/92* | (2006.01) | |
| *A61Q 17/04* | (2006.01) | |
| *A61Q 19/00* | (2006.01) | |
| *A61Q 19/08* | (2006.01) | |

(52) U.S. Cl.
CPC ................ *A61K 8/062* (2013.01); *A61K 8/11* (2013.01); *A61K 8/25* (2013.01); *A61K 8/73* (2013.01); *A61K 8/8152* (2013.01); *A61K 8/898* (2013.01); *A61K 8/922* (2013.01); *A61Q 17/04* (2013.01); *A61Q 19/007* (2013.01); *A61Q 19/08* (2013.01); *A61K 2800/41* (2013.01); *A61K 2800/42* (2013.01); *A61K 2800/594* (2013.01); *A61K 2800/624* (2013.01)

(58) Field of Classification Search
CPC ...... A61K 2800/62; A61K 8/922; A61K 8/73; A61K 2800/594; A61K 8/8152; A61K 8/898; A61K 2800/65; A61K 2800/624; A61K 8/11; A61K 8/925; A61K 2800/41; A61K 8/062; A61K 2800/42; A61K 8/25; A61K 2800/522; A61Q 9/08; A61Q 19/007; A61Q 17/04; A61Q 5/00; A61Q 19/00

See application file for complete search history.

(56) References Cited

U.S. PATENT DOCUMENTS

| | | |
|---|---|---|
| 9,993,398 B2 | 6/2018 | Goutayer et al. |
| 10,300,006 B2 | 5/2019 | Goutayer et al. |
| 2006/0204469 A1* | 9/2006 | Spengler .................. A61K 8/06 424/70.31 |
| 2007/0185281 A1 | 8/2007 | Song et al. |
| 2011/0110993 A1* | 5/2011 | Chieffi .................... A61K 8/731 424/401 |
| 2013/0195773 A1* | 8/2013 | Kindel ................. A61K 8/4973 424/49 |
| 2014/0045949 A1* | 2/2014 | Goutayer ............. A61K 8/8147 514/772.6 |

FOREIGN PATENT DOCUMENTS

| | | | |
|---|---|---|---|
| CN | 103635252 A | 3/2014 | |
| EP | 1386600 A1 * | 2/2004 | ............... A61Q 1/06 |
| FR | 3012050 A1 | 4/2015 | |
| WO | WO 2012/120043 A2 | 9/2012 | |
| WO | WO 2015/055748 A1 | 4/2015 | |

OTHER PUBLICATIONS

International Search Report dated Mar. 22, 2017 in International Application No. PCT/EP2017/053063.
Written Opinion in International Application No. PCT/EP2017/053063.
Search Report for French Application No. FR 1651172 dated Jun. 17, 2016.
Lubrizol, "Merquat™ 550 Polymer"; Safety Data Sheet, SDS_US—Merquat™ 550 Polymer; pp. 1-9, Feb. 19, 2016.
Tinci, "Cationic Starch"; Doc No. TC-MM 技术服务 one page, Version: A/0; last version date: Jan. 28, 2013.
Azelis, "Luviquat Supreme AT 1"; BASF Personal Care—Ross Organic an Azelis company; https://rossorg.com/product/luviquat-supreme-at-1/; pp. 1-3; Mar. 27, 2023.
Stepan S., "Pearlescent Conditioning Shampoo and Body Wash"; Formulation, Revision Date: Dec. 19, 2016 Publication Date: Mar. 7, 2008 © 2016, Stepan Company.
Dow, "Ucare™ Polymer JR-400", https://www.dow.com/en-us/pdp.ucare-polymer-jr-400.084959z.html#overview, pp. 1-3, Mar. 23, 2023.

(Continued)

*Primary Examiner* — Jianfeng Song
(74) *Attorney, Agent, or Firm* — Pearne & Gordon LLP

(57) ABSTRACT

The present invention relates to a composition, in particular cosmetic, in the form of an oil-in-water emulsion, comprising a continuous aqueous phase and a dispersed oil phase in the form of drops (G1) and drops (G2), wherein the size of the drops (G1) is less than 500 μm and the size of the drops (G2) is greater than 500 μm.

20 Claims, No Drawings

(56) References Cited

OTHER PUBLICATIONS

Chembk, "1,3-Bis(dimethylamino)propane", https://www.chembk.com/en/chem/1,3-Bis(dimethylamino)propane; pp. 1-3, Mar. 27, 2023.
Solvay, "Jaguar®"; https://www.solvay.com/en/product/jaguar-c-17; pp. 1-4, Mar. 27, 2023.
Solvay, "Mirapol® A 15"; https://www.solvay.com/en/product/mirapol-15; pp. 1-4, Mar. 27, 2023.
Lubrizol, "Merquat™ 550PR Polymer"; Technical Data Sheet; TDS-821, pp. 1-2; Feb. 23, 2012.
Universal Selector, "Lamequat® L Properties"; http://cosmetics.specialchem.com; pp. 1-2, May 7, 2021.
Amodimethicone, SpecialChem, The material selection platform, https://cosmetics.specialchem.com/inci-ingredients/amodimethicone#:~: text=Its%20chemical%20formula%20is%20C,on%20the%20hair%20or%20skin, (2023).

\* cited by examiner

OIL-IN-WATER EMULSIONS OF WHICH THE OIL PHASE IS IN THE FORM OF A MIXTURE OF DROPS OF DIFFERENT SIZES

The object of the present invention is oil-in-water emulsions whose oil phase is in the form of a mixture of drops of different sizes, as well as their methods of preparation.

The present invention also relates to the cosmetic use of the above-mentioned emulsions.

To date, dispersions of drops of an oil phase dispersed in an aqueous phase are, in particular, described in the applications WO2012/120043, FR2972367 and FR2976824. These dispersions are obtained, in particular, using a microfluidic procedure.

To improve the mechanical strength of such dispersions, the Applicant has developed stable dispersions of drops in which a gelling agent has been added to the dispersed oil phase.

However, there are difficulties in formulating such drops, in particular when gelled, in certain types of cosmetic compositions.

In fact, cosmetic compositions in emulsion form require the use of more or less high amounts of surfactants to ensure a satisfactory stability of the emulsions.

However, as shown below, it has been observed that the presence of surfactant(s) in a cosmetic cream in emulsion form comprising the aforementioned drops, in particular when gelled, causes instability of the drops. More particularly, there is substantial compositional maturation resulting in a migration of a portion of the oily phase of the above-mentioned drops to the micelles of surfactants located in the cream. This has the effect of reducing the size of the drops and, in the case of the gelled drops, an increase in their hardness (increase of the local concentration of oily gelling agent), which strongly degrades the organoleptic properties of the composition.

There is therefore a need for cosmetic compositions, especially "rich" creams (in particular having a high oil content, i.e. greater than 10% by weight relative to the total weight of the composition), which, in the presence of drops, in particular gelled drops, do not cause instability of the incorporated drops.

The object of the present invention is therefore to provide a composition, in particular a cosmetic composition, comprising drops, in particular gelled drops, making it possible to avoid the aforementioned compositional maturation phenomenon.

The present invention also aims to provide a composition comprising drops, in particular gelled drops, whose organoleptic properties are maintained, even in rich creams, and offer visual attractiveness.

The present invention also aims to provide a composition comprising drops which allow prolonged microdiffusion for a continuous action of active agents in the heart of the skin, in particular moisturizing agents and/or anti-aging agents.

The present invention also aims to provide a composition comprising drops, in particular gelled drops, for maintaining the mechanical strength of the drops.

Moreover, the provision of cosmetic compositions with a visual aspect and a novel feeling upon application, remains a constant goal.

Thus, the present invention relates to a composition, in particular a cosmetic composition, in the form of an oil-in-water emulsion, comprising a continuous aqueous phase and a dispersed oil phase in the form of drops (G1) and (G2), wherein:

the drops (G1) comprise an oil phase and a shell formed of at least one anionic polymer (PA1) and at least one cationic polymer (PC1), wherein the size of the drops (G1) is less than 500 µm, and the drops (G2) comprise an oil phase and a shell, wherein the shell is formed by at least one anionic polymer (PA2), identical to or different from (PA1), and at least one cationic polymer (PC2), identical to or different from (PC1), wherein the size of the drops (G2) is greater than 500 µm.

Preferably, the drops (G2) further comprise at least one gelling agent.

The compositions according to the invention therefore comprise an oil phase in the form of a mixture of drops whose size ranges are different. As explained below, the dispersed oil phase corresponds to a mixture of small drops (G1), possibly gelled, and large drops (G2), preferably gelled.

The compositions according to the invention may also be described as comprising drops (G2), or large drops, in a continuous phase comprising drops (G1), or small drops, as defined above. Thus, the compositions according to the invention may be characterized as an oil-in-water emulsion comprising at least two oil phases, wherein the first oil phase is represented by the drops (G1) while the second oil phase is represented by the drops (G2), preferably gelled.

The compositions according to the invention are therefore mixtures of populations of drops of different sizes, which constitute galenic originality, especially in the cosmetics field.

A composition according to the invention is particularly advantageous visual and sensory aspect.

Visually, the consumer is faced with a composition comprising drops (G2) visible to the naked eye. The significance of this attractive visual aspect is further enhanced when at least the drops (G2) are colored.

At the sensory level, the texture of the compositions according to the invention differs from "conventional" emulsions stabilized by surfactants. In fact, the presence of the drops (G1) gives a unique texture that is light and voluble and involves an application in two stages. More particularly, the emulsion formed by the drops (G1) spreads easily on the skin. The first moments of application are very aqueous with a marked brittle effect. Then, the feeling evolves towards an oily veil that fades to leave a light and hydrated skin. This texture is particularly advantageous and surprising to the those skilled in the art in view of the absence of surfactants in these emulsions.

Likewise, the application to a keratinous material, in particular the skin, of a composition according to the invention leads at the moment of its spreading to a shearing of the drops (G2). The sensory effect provided by this application is reflected by literally feeling the drops (G2) melt, as it were, under the effect of spreading with an enhanced oily effect. This sensory effect is further enhanced when the drops (G2) are gelled.

In the context of the present invention, the above-mentioned emulsions may be denoted by the term "dispersions".

A drop according to the invention is composed of a core, also called the interior of the drop, surrounded by a shell, which isolates the inside of the drop from the continuous phase of the emulsion.

Advantageously, the pH of a composition according to the invention is typically from 5.0 to 7.0.

Size of the (G1) and (G2) Drops

In the context of the present invention, the term "size" designates the diameter, in particular the mean diameter, of the drops (G1) and (G2).

The oil phase of the compositions according to the invention therefore consists of a combination of drops (G1) and (G2) of different sizes. The drops (G1) may be designated as drops of small size (or small drops), and the drops (G2) as drops of large size (or large drops).

According to the invention, the size of the drops (G1) is less than 500 µm, preferably less than 400 µm, in particular less than 300 µm, better still less than 200 µm, particularly less than 100 µm, even less than 20 µm, and better still less than 10 µm. Preferably, the size of the drops (G1) is between 0.1 and 200 µm, preferably between 0.25 and 100 µm, in particular between 0.5 µm and 50 µm, preferably between 1 µm and 20 µm, and better still between 1 µm and 10 µm, even better between 3 µm and 5 µm.

These drops of reduced size have an effect on the texture. In fact, a composition, formed of finely dispersed drops, has improved lubricity qualities.

According to the invention, the size of the drops (G2) is greater than 500 µm, preferably greater than 600 µm, in particular greater than 700 µm, and better still greater than 800 µm. Preferably, the size of the drops (G2) is between 500 µm and 3000 µm, preferably between 510 µm and 2500 µm, better still between 600 µm and 2000 µm, and more particularly between 700 µm and 1200 µm.

Preferably, the drops (G2), or even the drops (G1), have a uniform size distribution. Preferably, the drops (G2) form a population of monodisperse drops, in particular wherein they have a mean diameter of from 500 µm to 3000 µm, and a coefficient of variation Cv less than 10%, or even less than 3%.

In the context of the present description, the term "monodisperse drops" is understood to mean that the population of drops of the dispersed phase according to the invention has a uniform size distribution. Monodisperse drops have good monodispersity. Conversely, drops with poor monodispersity are said to be "polydispersed".

According to one embodiment, the mean diameter $\overline{D}$ of the drops is, for example, measured by analysis of a photograph of a batch consisting of N drops, by image processing software (Image J). Typically, according to this method, the diameter is measured in pixels, then given in µm, depending on the size of the container containing the drops of the dispersion.

Preferably, the value of N is chosen to be greater than or equal to 30, so that this analysis reflects the drop diameter distribution of the emulsion in a statistically significant manner.

The diameter Di of each drop is measured, and the average diameter $\overline{D}$ obtained by calculating the arithmetic mean of these values:

$$\overline{D} = \frac{1}{N}\sum_{i=1}^{N} D_i$$

The standard deviation σ of the diameters of the drops of the dispersion may be obtained from these values Di:

$$\sigma = \sqrt{\frac{\sum_{i=1}^{N}(D_i - \overline{D})^2}{N}}$$

The standard deviation σ of a dispersion reflects the distribution of the diameters Di of the drops of the dispersion around the mean diameter $\overline{D}$.

By knowing the mean diameter and standard deviation σ of a dispersion, it may be determined that 95.4% of the drop population is found in the diameter range [$\overline{D}$−2σ; $\overline{D}$+2σ] and that 68.2% of the population is found in the range [$\overline{D}$−σ; $\overline{D}$+σ].

To characterize the monodispersity of the dispersion according to this embodiment of the invention, the coefficient of variation may be calculated:

$$C_v = \frac{\sigma}{\overline{D}}$$

This parameter reflects the distribution of the diameters of the drops as a function of the average diameter thereof.

The coefficient of variation Cv of the diameters of the drops according to this embodiment of the invention is less than 10%, preferably less than 5%, or even less than 3%.

Alternatively, the monodispersity may be demonstrated by placing a sample of a composition according to the invention in a bottle of constant circular section. A gentle stirring is performed by rotating a quarter of a turn for half a second around the axis of symmetry passing through the bottle, followed by a rest of half a second, before repeating the operation in the opposite direction, and four times in a row.

The drops (G2) are organized in a crystalline form when they are monodispersed. Thus, they present a stack in a repeating pattern in three dimensions. It is then possible to observe that a regular stack indicates good monodispersity, while an irregular stack reflects the polydispersity of the dispersion.

Advantageously, a composition according to the invention may comprise from 1% to 50%, preferably from 3% to 40%, and better still from 5% to 30%, by weight of drops (G1) relative to the total weight of the composition.

Advantageously, a composition according to the invention may comprise from 0.5% to 40%, in particular from 1% to 30%, preferably from 2% to 20%, and more preferably from 3% to 15%, or even 5% to 10% by weight of drops (G2) relative to the total weight of the composition.

Advantageously, a composition according to the invention may comprise a weight ratio "drops (G1)/drops (G2)" of between 0.025 and 100, in particular between 0.03 and 50, preferably between 0.15 and 20, and better still between 0.33 and 10.

Viscosity

The viscosity of the compositions according to the invention may vary significantly, which therefore makes it possible to obtain varied textures.

According to one embodiment, a composition according to the invention has a viscosity of from 1 mPa·s to 500,000 mPa·s, preferably from 10 to 300,000 mPa·s, and better still from 1,000 mPa·s to 100,000. mPa·s as measured at 25° C.

According to one embodiment, the aqueous phase of a composition according to the invention, at ambient temperature and atmospheric pressure, has a viscosity of from 1 mPa·s to 500,000 mPa·s, preferably from 10 to 300,000 mPa·s, and better still from 1,000 mPa·s to 100,000 mPa·s as measured at 25° C.

According to one embodiment, the oil phase represented by the drops (G1) of a composition according to the invention, at ambient temperature and atmospheric pressure, has a viscosity of from 0.1 mPa·s to 1,000,000 mPa·s. preferably from 0.5 mPa·s to 500,000 mPa·s, and more preferably from 1 mPa·s to 1000 mPa·s, as measured at 25° C.

According to one embodiment, the oil phase represented by the drops (G2) of a composition according to the invention, at ambient temperature and atmospheric pressure, has a viscosity of between 20,000 mPa·s and 100,000,000 mPa·s, preferably from 50,000 mPa·s to 1,000,000 mPa·s, and more preferably from 100,000 mPa·s to 500,000 mPa·s at 25° C.

For reasons of technical feasibility, particularly in view of the manufacturing processes of the compositions according to the invention as described below, the viscosity of the emulsion comprising the drops (G1) is designed to ensure homogenization, or even manufacture, of drops (G2) in the emulsion comprising the drops (G1), and thus the manufacture of a composition according to the invention.

In view of the technical elements provided in the present description, this design falls within the expertise of those skilled in the art.

If possible and if necessary, those skilled in the art may enhance the viscosity of the composition according to the invention, in particular the viscosity of the continuous aqueous phase, by adding a solution to increase the viscosity. Preferably, this viscosity-increasing solution comprises a base, in particular an alkali metal hydroxide, such as sodium hydroxide, as further described below.

The viscosity is measured at ambient temperature, for example T=25° C.±2° C. and at ambient pressure, for example 1013 mbar, by the method described below.

A Brookfield type viscometer, typically a Brookfield RVDV-E digital viscometer (spring twist torque of 7187.0 dyne-cm) is used which is a rotational velocity viscometer provided with a spindle. A speed is imposed on the spindle in rotation and the measurement of the torque exerted on the spindle makes it possible to determine the viscosity by knowing the geometry/shape parameters of the spindle used.

For example, a size No. 04 spindle (Brookfield reference: RV4) is used. The shear rate corresponding to the measurement of the viscosity is defined by the spindle used and the speed of rotation thereof.

The viscosity measurement is carried out for 1 minute at room temperature (T=25° C.±2° C.). About 150 g of solution are placed in a beaker of 250 ml volume, having a diameter of about 7 cm so that the height of the volume occupied by the 150 g of solution is sufficient to reach the graduation marked on the spindle. Then, the viscometer is started at a speed of 10 rpm and the value displayed on the screen is expected to be stable. This measurement gives the viscosity of the tested fluid, as mentioned in the context of the present invention.

Oil Phase

As indicated above, the dispersed oil phase of the compositions of the invention is a mixture of different drops (G1) and (G2).

These drops are of different sizes but may be identical or different in nature, in particular as regards the nature of the anionic and cationic polymers, or oils and/or additional compounds and/or active agents described below.

Oil(s)

According to one embodiment, the oil phase of the drops (G1) and/or (G2) may comprise at least one oil (H1) in which the cationic polymers (PC1) and (PC2) are soluble. In fact, the composition according to the invention may comprise at least one oil compatible with the cationic polymers (PC1) and (PC2). The oil (H1), therefore, corresponds to a good solvent for the cationic polymers (PC1) and (PC2).

The drops (G1) and/or (G2) according to the invention may comprise a single oil (H1) or a mixture of several oils (H1). A drop (G1) and/or (G2) according to the invention may therefore comprise at least one, at least two, at least three, at least four, at least five or more oil(s) (H1) as described below.

The term "oil" is understood to mean a fatty substance that is liquid at room temperature (25° C.).

According to one embodiment, the oil (H1) of the drops (G1) may be identical to or different from the oil (H1) of the drops (G2). Likewise, when the drops (G1) comprise a mixture of oils (H1), the mixture of oils (H1) of the drops (G2) may be identical or different.

According to one embodiment, the drops (G1) may comprise a single oil (H1) while the drops (G2) may comprise a mixture of oils (H1), and vice versa.

As oils (H1) according to the invention, may be mentioned for example:
- hydrocarbon oils of animal origin, such as perhydrosqualene and squalane;
- synthetic esters and ethers, in particular of fatty acids, such as the oils of formulas $R_1COOR_2$ and $R_1OR_2$, in which $R_1$ represents the residue of a $C_8$ to $C_{29}$ fatty acid, and $R_2$ represents a hydrocarbon chain, branched or unbranched, with $C_3$ to $C_{30}$, such as, for example, purcellin oil, isononyl isononanoate, isodecyl neopentanoate, isostearyl neopentanoate, isopropyl myristate, octyldodecyl myristate, ethyl palmitate-2-hexyl, octyl-2-dodecyl stearate, octyl-2-dodecyl erucate, isostearyl isostearate; hydroxylated esters such as isostearyl lactate, octyl hydroxystearate, octyldodecyl hydroxystearate, diisostearyl malate, triisocetyl citrate, heptanoates, octanoates, decanoates of fatty alcohols; polyol esters, such as propylene glycol dioctanoate, neopentyl glycol diheptanoate and diethylene glycol diisononanoate; and pentaerythritol esters such as pentaerythrityl tetrahehenate (DUB PTB) or pentaerythrityl tetraisostearate (Prisorine 3631);
- linear or branched hydrocarbons of mineral or synthetic origin, such as paraffin oils, volatile or not, and their derivatives, petroleum jelly, polydecenes, hydrogenated polyisobutene such as parleam oil;
- silicone oils, for example volatile or non-volatile polymethylsiloxanes (PDMSs) with a linear or cyclic silicone chain, which are liquid or pasty at room temperature, in particular cyclopolydimethylsiloxanes (cyclomethicones) such as cyclohexasiloxane and cyclopentasiloxane; polydimethylsiloxanes (or dimethicones) comprising alkyl, alkoxy or phenyl groups, within or at the end of the silicone chain, groups having from 2 to 24 carbon atoms; phenyl silicones such as phenyltrimethicones, phenyldimethicones, phenyltrimethylsiloxydiphenylsiloxanes, diphenyl-dimethicones, diphenylmethyldiphenyltrisiloxanes, 2-phenylethyltrimethylsiloxysilicates, and polymethylphenylsiloxanes;
- fatty alcohols having from 8 to 26 carbon atoms, such as cetyl alcohol, stearyl alcohol and their mixture (cetylstearyl alcohol), or else octyldodecanol;
- partially fluorinated hydrocarbon oils and/or silicone oils such as those described in document JP-A-2-295912;
- and their mixtures.

According to one embodiment, the oil (H1) is chosen from esters of formula $R_1COOR_2$, in which $R_1$ represents the residue of a $C_8$ to $C_{29}$ fatty acid, and $R_2$ represents a hydrocarbon chain, branched or unbranched, with $C_3$ to $C_{30}$.

According to one embodiment, the oil (H1) is chosen from fatty alcohols having from 8 to 26 carbon atoms.

According to one embodiment, the oil (H1) is chosen from hydrocarbon oils having from 8 to 16 carbon atoms, and in particular $C_8$-$C_{16}$ branched alkanes (also known as isoparaffins or isoalkanes), such as isododecane (also called 2,2,4,4,6-pentamethylheptane), isodecane, isohexadecane, and, for example, the oils sold under the trade names Isopars® or Permethyls®.

According to a preferred embodiment, the oil (H1) is chosen from the group consisting of isononyl isononanoate, dimethicone, isohexadecane, polydimethylsiloxane, octyldodecanol, isodecyl neopentanoate, isostearyl neopentanoate and mixtures thereof.

According to another preferred embodiment, the oil (H1) is chosen from silicone oils. Preferably, the oil phase of the drops (G1) and/or (G2) does not include oils other than silicone oils. Preferably, the oils present in the oil phase of the drops (G1) and/or (G2) are silicone oils.

Preferably, the oil (H1) is isononyl isononanoate.

According to one embodiment, the oil (H1) is not a plant oil.

According to one embodiment, the oil (H1) is not a silicone oil, and preferably is not selected from polydimethylsiloxanes (PDMS).

According to a preferred embodiment, the oil (H1) which may be present in the drops (G2) according to the invention is not a silicone oil or a fluorinated oil.

According to a preferred embodiment, the drops (G2) according to the invention may comprise at least one silicone oil or a fluorinated oil, provided that it also comprises at least one oil (H1) as described above but different from a silicone oil or a fluorinated oil.

According to a preferred embodiment, the drops (G1) and (G2) comprise isononyl isononanoate.

According to a preferred embodiment, the drops (G1) and/or (G2) according to the invention comprise at least 1% by weight of oil(s) (H1), preferably isononyl isononanoate, relative to the total weight of the composition.

According to another embodiment, a composition according to the invention, in particular the oil phase of the drops (G1) and/or (G2), does not comprise polydimethylsiloxane (PDMS), and preferably does not comprise any silicone oil.

According to another embodiment, a composition according to the invention does not comprise plant oil.

According to one embodiment, the content of oil(s) (H1) in a composition according to the invention is between 1% and 99.49%, preferably between 20% and 90%, and in particular between 50% and 80%, by weight relative to the total weight of the oil phase of the drops (G1) and/or (G2).

According to one embodiment, the oil phase of the drops (G1) and/or (G2) of the invention may further comprise at least one hydrocarbon oil of plant origin (H2). The oil phase of the drops (G1) and/or (G2) may comprise several oils (H2).

Preferably, according to the invention, the following compounds are used as oil(s) (H2): caprylic and capric acid triglycerides, caprylic, capric, myristic and stearic acid triglycerides (INCI name: Caprylic/capric/myristic/stearic triglyceride), triethylhexanoine, meadow-foam seedling oil Limnanthes Alba (INCI name: Limnanthes Alba (Meadowfoam) Seed Oil), macadamia nut oil (INCI name: Macadamia *Ternifolia* Seed Oil), rosehip oil Rosa *Canina* (INCI name: *Rosa Canina* Fruit Oil), soybean oil (INCI name: *Glycine Soja* (Soybean) Oil), sunflower seed oil (INCI name: *Helianthus Annuus* (Sunflower) Seed Oil), tribehenin (INCI name: tribehenin), triisostearin (INCI name: triisostearin), apricot kernel oil (INCI name: *Prunus Armeniaca* (Apricot) Kernel Oil), rice bran (INCI name: *Oryza Sativa* (Rice) Bran Oil), argan oil (INCI name: *Argania Spinosa* Kernel Oil), avocado oil (INCI name: *Persea* Gratissiman oil), evening primrose oil (INCI name: *Oenothera Biennis* Oil), rice germ oil (INCI name: *Oryza Sativa* Germ Oil), hydrogenated coconut oil (INCI name: Hydrogenated Coconut Oil), sweet almond oil (INCI name: *Prunus Amygdalus Dulcis* Oil), sesame seed oil (INCI name: *Sesamum Indicum* Seed Oil), Hydrogenated Rapeseed Oil (INCI Name: Hydrogenated Rapeseed Oil), Safflower Seed Oil (INCI name: *Carthamus Tinctorius* Seed Oil), Queensland nut oil Macadamia *integrifolia* (INCI name: Macadamia *Integrifolia* Seed Oil), tricaprylin (or triacylglycerol), wheat germ oil (INCI name: *Triticum Vulgare* Germ Oil), borage seed oil (INCI name: *Borago Officinalis* Seed Oil), shean oil (INCI name: *Butyrospermum Parkii* Oil), hydrogenated castor oil (INCI name: Hydrogenated Castor Oil), chinese cabbage seed oil (INCI name: *Brassica Campestris* Seed Oil), camellian oil, and, in particular, *camellia* seed from Japan (INCI name: *Camellia Japonica* Seed Oil), green tea seed oil (INCI name: *Camellia Sinensis* Seed Oil), Sea Buckthorn Oil (INCI name: *Hippophae Rhamnoides* Oil), Camellia Kissi seed oil (INCI name: *Camellia Kissi* Seed Oil), *Moringa* Seed Oil (INCI name: *Moringa Pterygosperma* Seed Oil), canolan oil (INCI name: Canolan oil), tea seed oil (INCI name: *Camellia* Oleifera Seed Oil), carrot seed oil (INCI name: *Daucus Carota Sativa* Seed Oil), triheptanoine (INCI name: Triheptanoin), vanillan oil (INCI name: *Vanilla Planifolia* Fruit Oil), glycerides of canolan oil and phytosterols (INCI name: Phytosteryl Canola Glycerides), soybean oil cassissier (INCI name: *Ribes Nigrum* (Black Currant) Seed Oil), karanja seed oil (INCI name: Pongamia *Glabra* Seed Oil), Roucou (INCI name: Roucou (*Bixa orellana*) Oil), and mixtures thereof.

Preferably, the oil (H2) is chosen from vegetable oils rich in polyunsaturated fatty acids.

For the purposes of the present invention, the term "unsaturated fatty acid" is understood to mean a fatty acid comprising at least one double bond.

According to a preferred embodiment, unsaturated fatty acids containing from 18 to 22 carbon atoms, in particular polyunsaturated fatty acids, especially ω-3 and ω-6 fatty acids, are used as oil (H2).

Among the polyunsaturated fatty acids of the ω-6 series, mention may, in particular, be made of linoleic acid with 18 carbon atoms and two unsaturations (18:2, ω-6), γ-linolenic acid with 18 carbon atoms. and three unsaturations (18:3, ω-6), dihomogamalinolenic acid with 20 carbon atoms and 3 unsaturations (20:3, ω-6), arachidonic acid, acid 5,8,11,14 eicosatetraenoic (20:4, ω-6) and docosatetraenoic acid (22:4, ω-6).

The polyunsaturated fatty acids of the ω-3 series may, in particular, be chosen from α-linolenic acid (18:3, ω-3), stearidonic acid (18:4, ω-3), acid 5,8,11,14,17-eicosapentaenoic or EPA (20:5, ω-3), and 4,7,10,13,16,19-docosahéxaenoic acid or DHA (22:6, ω-3), docosapentanoic acid (22:5, ω-3), n-butyl-5,11,14-eicosatrienonic acid.

According to one embodiment, the content of oil(s) (H2) in the oil phase of the drops (G1) and/or (G2) of a composition according to the invention is between 0% and 40%, preferably between 0.1% and 25%, and, in particular, between 1% and 20%, by weight relative to the total weight of the fat phase of the composition.

According to one embodiment, the mass ratio between the amount of oil(s) (H1) and the amount of oil(s) (H2) ranges from 0.025 to 99.99, preferably from 0.8 to 90, and in particular from 2.5 to 80.

The oil phase may also comprise at least one other oil that is different from the oils (H1) and (H2).

A composition according to the invention may comprise from 0.0001% to 50%, preferably from 0.1% to 40%, and better still from 1% to 25%, by weight of oil(s) relative to the total weight of the composition.

Advantageously, the oil phase of the drops (G2) and/or (G1) comprises at least one oil having a refractive index close to that of the aqueous continuous phase, namely an oil having a refractive index, at ambient temperature (25° C.) and atmospheric pressure, preferably between 1.2 and 1.6, preferably between 1.25 and 1.5, in particular between 1.3 and 1.4. This embodiment is advantageous in that it makes it possible to improve the transparency of the oil phase of the drops (G2) and/or (G1), and therefore the transparency of the composition according to the invention. Advantageously, the oil having a refractive index of between 1.2 and 1.6 is a silicone oil, in particular a phenyl silicone oil.

Gelling Agent

As indicated above, the oil phase of the drops (G2) may further comprise at least one gelling agent. It may therefore comprise a single gelling agent or a mixture of gelling agents. Preferably, the oil phase of the drops (G2) comprises at least one gelling agent.

Such a gelling agent is different from the anionic and cationic polymers described above.

In the context of the invention, and unless otherwise stated, the term "gelling agent" is understood to mean an agent for increasing the viscosity of the oil phase of the drops (G2) devoid of the gelling agent, and to reach a final viscosity of the gelled oil phase greater than 20,000 mPa·s, preferably greater than 50,000 mPa·s, better still greater than 100,000 mPa·s, and more particularly greater than 200,000 mPa·s.

The choice of gelling agent(s) takes place especially with regard to the nature of the dispersed phase. Thus, for reasons of compatibility, the gelling agent is lipophilic.

According to one embodiment, only the drops (G2) comprise at least one gelling agent. In other words, according to this embodiment, the drops (G1) are devoid of gelling agent.

According to another embodiment, the drops (G2) and (G1) comprise at least one gelling agent, which is identical or different.

According to one embodiment, the gelling agent is chosen from the group consisting of organic, inorganic, polymeric or molecular lipophilic gelling agents; solid fats that are solid at ambient temperature and pressure, especially chosen from waxes, pasty fatty substances, butters; and their mixtures.

Lipophilic Gelling Agent(s)

The gelling agents that may be used according to the invention may be organic or inorganic, polymeric or molecular lipophilic gelling agents.

According to one embodiment, the gelling agent is chosen from the group consisting of modified clays, silicas, such as fumed silica, and mixtures thereof.

As inorganic lipophilic gelling agents, may be mentioned optionally modified clays, such as hectorites modified with a $C_{10}$ to $C_{22}$ ammonium chloride, such as hectorite modified with di-stearyl dimethyl ammonium chloride such as, for example, the product sold under the name Bentone 38V® by the company ELEMENTIS. Mention may also be made of hectorite modified with distearyldimethylammonium chloride, also known as quaternium-18 bentonite, such as the products marketed or manufactured under the names Bentone 34 by the company Rheox, Claytone XL, Claytone 34 and Claytone 40 marketed or manufactured by Southern Clay, modified clays known as benzalkonium and quaternium-18 bentonites and marketed or manufactured under the names Claytone HT, Claytone GR and Claytone PS by Southern Clay, clays modified by chloride of stearyldimethylbenzoylammonium, known as steralkonium bentonites, such as the products marketed or manufactured under the names Claytone APA and Claytone AF by Southern Clay, and Baragel 24 sold or manufactured by Rheox.

Mention may also be made of fumed silica optionally treated with a hydrophobic surface whose particle size is less than 1 µm. It is in fact possible to chemically modify the surface of the silica, wherein chemical reaction generates a decrease in the number of silanol groups present on the surface of the silica. In particular, it is possible to substitute silanol groups with hydrophobic groups in order to obtain a hydrophobic silica.

The hydrophobic groups may be:

trimethylsiloxyl groups, which are obtained, in particular, by treating fumed silica in the presence of hexamethyldisilazane. Silicas thus treated are called "silica silylate" according to the CTFA (8th edition, 2000). They are for example marketed under the references Aerosil R812® by the company DEGUSSA, CAB-O-SIL TS-530® by the company CABOT; or dimethylsilyloxyl or polydimethylsiloxane groups, which are especially obtained by treating fumed silica in the presence of polydimethylsiloxane or dimethyldichlorosilane. Silicas thus treated are called "silica dimethyl silylate" according to the CTFA (8th edition, 2000). They are for example marketed under the references Aerosil R972®, and Aerosil R974® by the company DEGUSSA, CAB-O-SIL TS-610® and CAB-O-SIL TS-720® by the company CABOT.

The hydrophobic fumed silica has, in particular, a particle size that may be nanometric to micrometric, for example ranging from about 5 to 200 nm.

It is also possible to mention hydrophobic silica aerogels, preferably silylated silica (INCI name: silica silylate). Concerning the preparation of hydrophobic silica aerogel particles surface-modified by silylation, reference may be made to U.S. Pat. No. 7,470,725. Examples of hydrophobic silica aerogels that may be used in the invention include, for example, the aerogel marketed under the name VM-2260 or VM-2270 (INCI name: silica silylate), by the company Dow Corning. Also may be mentioned aerogels sold by the company Cabot under the references Aerogel TLD 201, Aerogel OGD 201, Aerogel TLD 203, ENOVA Aerogel MT 1100, ENOVA Aerogel MT 1200.

Polymeric organic lipophilic gelling agents are, for example, partially or fully crosslinked elastomeric organopolysiloxanes of three-dimensional structure, such as those marketed under the names KSG6®, KSG16® and KSG18® by the company SHIN-ETSU, Trefil E-505C® and Trefil E-506C® by the company DOW-CORNING, Gransil SR-CYC®, SR DMF10®, SR-DC556®, SR 5CYC Gel®, SR DMF 10 Gel® and SR DC 556 Gel® by the company GRANT INDUSTRIES, SF 1204° and JK 113° by the company GENERAL ELECTRIC; ethylcellulose such as that sold under the name Ethocel® by the company Dow Chemical; galactomannans having from one to six, and in particular from two to four, hydroxyl groups, substituted by a saturated or unsaturated alkyl chain, such as guar gum alkylated by $C_1$-$C_6$ alkyl chains, and in particular C1 to C3 and mixtures thereof. Block copolymers of the "diblock", "triblock" or "radial" type of the polystyrene/polyisoprene, polystyrene/polybutadiene type, such as those sold under the name Luvitol HSB® by the company BASF, of the polystyrene/copoly (ethylene-propylene) type such as those sold under the name Kraton® by the company Shell Chemical Co. or else of the polystyrene/copoly (ethylene-butylene) type, mixtures of triblock and radial (star) copolymers in isododecane, such as those marketed by the company PENRECO under the name Versagel® such as the mixture of butylene/ethylene/styrene triblock copolymer and star copolymer ethylene/propylene/styrene in isododecane (Versagel M 5960).

According to one embodiment, the gelling agent that may be used according to the invention is chosen from the group consisting of polyacrylates, esters of dextrin and of fatty acid(s), esters of glycerol and fatty acid(s), polyamides, and mixtures thereof.

Lipophilic gelling agents which may also be mentioned are polymers having a weight average molecular weight of less than 100,000, comprising a) a polymer backbone having hydrocarbon-based repeating units provided with at least one heteroatom, and optionally b) at least one pendant fatty chain and/or at least one optionally functionalized fatty chain having from 6 to 120 carbon atoms and bonded to these hydrocarbon units, as described in applications WO 02/056847, WO 02/47619, in particular the resins of polyamides (in particular comprising alkyl groups having from 12 to 22 carbon atoms) such as those described in U.S. Pat. No. 5,783,657.

As an example of a polyamide resin that may be used according to the present invention, mention may be made of Uniclear 100 VG® marketed by the company ARIZONA CHEMICAL.

It is also possible to use polyorganosiloxane-type silicone polyamides such as those described in U.S. Pat. Nos. 5,874,069, 5,919,441, 6,051,216 and 5,981,680.

These silicone polymers may belong to the following two families:
 polyorganosiloxanes comprising at least two groups capable of establishing hydrogen interactions, wherein these two groups are located in the polymer chain, and/or
 polyorganosiloxanes comprising at least two groups capable of establishing hydrogen interactions, wherein these two groups are located on grafts or branches.

According to one embodiment, the lipophilic gelling agent is an ester of dextrin and of fatty acid, such as dextrin palmitates.

According to one embodiment, the ester of dextrin and fatty acid(s) according to the invention is a mono-ester or poly-ester of dextrin and of at least one fatty acid corresponding to the following formula (II):

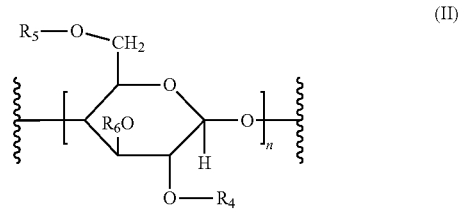

(II)

in which:
 n is an integer ranging from 2 to 200, preferably ranging from 20 to 150, and in particular ranging from 25 to 50,
 the radicals $R_4$, $R_5$ and $R_6$, which are identical or different, are chosen from hydrogen or an acyl group $—COR_a$ in which the radical $R_a$ represents a hydrocarbon radical, linear or branched, saturated or unsaturated, having from 5 to 50, or preferably from 5 to 25 carbon atoms, with the proviso that at least one of the $R_4$, $R_5$ and $R_6$ radicals is different from hydrogen.

According to one embodiment, $R_4$, $R_5$ and $R_6$ represent, independently of each other, H or an acyl group $—C(O)R_a$ in which $R_a$ is a hydrocarbon radical as defined above, provided that at least two of the radicals $R_4$, $R_5$ or $R_6$ are identical and different from hydrogen.

According to one embodiment, when the radicals $R_4$, $R_5$ and $R_6$, which are identical or different, represent a $—C(O)R_a$ radical, these may be chosen from the radicals caprylyl, caproyl, lauroyl, myristyl, palmityl and stearyl radicals, or eicosanyl, docosanoyl, isovaleryl, 2-ethylbutyryl, ethylmethylacetyl, isoheptanyl, 2-ethylhexanyl, isononanyl, isodecanyl, isotridecanyl, isomyristyl, isopalmityl, isostearyl, isohexanyl, decenyl, dodecenyl, tetradecenyl, myristyl, hexadecenoyl, palmitolyl, oleyl, elaidyl, eicosenyl, sorbyl, linoleyl, linolenyl, punicyl, arachidonyl, stearolyl, and mixtures thereof.

Among the esters of dextrin and fatty acid(s), mention may be made, for example, of dextrin palmitates, dextrin myristates, dextrin palmitates/ethylhexanoates and mixtures thereof.

Mention may, in particular, be made of the esters of dextrin and of fatty acid(s) marketed under the names Rheopearl® KL2 (INCI name: dextrin palmitate), Rheopearl® TT2 (INCI name: dextrin palmitate ethylhexanoate), and Rheopearl® MKL2 (INCI name: myristate dextrin) by the company Miyoshi Europe.

Compared to Rheopearl® KL2, Rheopearl MKL2 (INCI: Dextrin Myristate) is advantageous in that it leads to drops (G2), and therefore to a composition according to the invention, having an improved transparency.

According to one embodiment, the gelling agent is chosen from polyacrylates resulting from the polymerization of $C_{10}$ to $C_{30}$ alkyl acrylate(s), preferably of $C_{14}$-$C_{24}$ alkyl acrylate(s), and still more preferably $C_{18}$-$C_{22}$ alkyl acrylate(s).

According to one embodiment, the polyacrylates are polymers of acrylic acid esterified with a fatty alcohol whose saturated carbon chain comprises from 10 to 30 carbon atoms, preferably from 14 to 24 carbon atoms, or a mixture of the fatty alcohols. Preferably, the fatty alcohol comprises 18 carbon atoms or 22 carbon atoms.

Among the polyacrylates, may be mentioned more particularly stearyl polyacrylate, behenyl polyacrylate. Preferably, the gelling agent is stearyl polyacrylate or behenyl polyacrylate.

Also may be mentioned polyacrylates sold under the names Interlimer® (INCI name: Poly $C_{10}$-$C_{30}$ alkyl acrylate), including Interlimer® 13.1 and Interlimer® 13.6, by the company Airproducts.

According to one embodiment, the gelling agent is an ester of glycerol and fatty acid(s), in particular a mono-, dior triester of glycerol and fatty acid(s). Typically, the ester of glycerol and fatty acid(s) may be used alone or as a mixture.

According to the invention, it may be a glycerol ester and a fatty acid or a glycerol ester and a mixture of fatty acids.

According to one embodiment, the fatty acid is selected from the group consisting of behenic acid, isooctadecanoic acid, stearic acid, eicosanoic acid, and mixtures thereof.

According to one embodiment, the ester of glycerol and fatty acid(s) has the following formula (I):

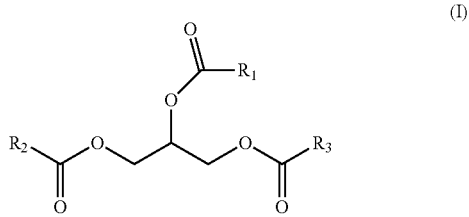

(I)

in which: $R_1$, $R_2$ and $R_3$ are, independently of one another, selected from H and a saturated alkyl chain comprising from 4 to 30 carbon atoms, wherein at least one of $R_1$, $R_2$ or $R_3$ is different from H.

According to one embodiment, $R_1$, $R_2$ and $R_3$ are different.

According to one embodiment, $R_1$, $R_2$ and/or $R_3$ represent(s) a saturated alkyl chain comprising from 4 to 30, preferably from 12 to 22, and preferably from 18 to 22 carbon atoms.

According to one embodiment, the ester of glycerol and of fatty acid(s) corresponds to a compound of formula (I) in which $R_1$=H, $R_2$=$C_{21}H_{43}$ and $R_3$=$C_{19}H_{40}$.

According to one embodiment, the ester of glycerol and of fatty acid(s) corresponds to a compound of formula (I) in which $R_1$=$R_2$=$R_3$=$C_{21}H_{43}$.

According to one embodiment, the ester of glycerol and of fatty acid(s) corresponds to a compound of formula (I) in which $R_1$=$R_2$=H, and $R_3$=$C_{19}H_{40}$.

According to one embodiment, the ester of glycerol and of fatty acid(s) corresponds to a compound of formula (I) in which $R_1$=$R_2$=H, and $R_3$=$C_{17}H_{35}$.

Mention may, in particular, be made of the esters of glycerol and of fatty acid(s) marketed under the names Nomcort HK-G (INCI name: Glyceryl behenate/eicosadioate) and Nomcort SG (INCI name: Glyceryl tribehenate, isostearate, eicosadioate), by the company Nisshin Oillio.

Solid Fatty Substances

The fatty substance that is solid at ambient temperature and pressure, different from the lipophilic gelling agents described above, is especially chosen from the group consisting of waxes, pasty fatty substances, butters and their mixtures.

Wax(es)

For the purposes of the invention, the term "wax" means a lipophilic compound, solid at ambient temperature (25° C.), with a reversible solid/liquid state change, having a melting point of greater than or equal to 30° C. up to 120° C.

The protocol for measuring this melting point is described below.

The waxes that may be used in a composition according to the invention are chosen from waxes, solid, deformable or not at ambient temperature, of animal, vegetable, mineral or synthetic origin, and mixtures thereof.

In particular, it is possible to use hydrocarbon-based waxes such as beeswax, lanolin wax, and Chinese insect waxes; rice wax, Carnauba wax, Candelilla wax, Ouricurry wax, Alfa wax, cork fiber wax, sugar cane wax, Japanese wax and sumac wax; montan wax, microcrystalline waxes, paraffins and ozokerite; polyethylene waxes, waxes obtained by Fisher-Tropsch synthesis, waxy copolymers and their esters, and mixtures thereof.

Mention may also be made of waxes obtained by catalytic hydrogenation of animal or vegetable oils having linear or branched $C_8$-$C_{32}$ fatty chains.

Among these, may be mentioned hydrogenated jojoban oil, hydrogenated sunflower oil, hydrogenated castor oil, hydrogenated coconut oil and hydrogenated lanolin oil, di-tetrastearate (trimethylol-1,1,1 propane) sold under the name "HEST 2T-4S" by the company HETERENE, di-(1,1-trimethylolpropane) tetraprenate sold under the name HEST 2T-4B by the company HETERENE.

It is also possible to use the waxes obtained by transesterification and hydrogenation of vegetable oils, such as castor oil or olive oil, such as the waxes sold under the names Phytowax ricin 16L64® and 22L73® and Phytowax Olive 18L57 by the company Sophim. Such waxes are described in application FR 2 792 190.

Mention may also be made of the waxes marketed under the names Kahlwax® 2039 (INCI name: Candelilla cera) and Kahlwax® 6607 (INCI name: *Helianthus Annuus* Seed Wax) by the company Kahl Wachsraffinerie, Casid HSA (INCI name: Hydroxystearic Acid) by the CFPA SACI company, Performa® 260 (INCI name: synthetic wax) and Performa® 103 (INCI name: synthetic wax) by the company New Phase, and AJK-CE2046 (INCI name: Cetearyl alcohol, dibutyl lauroyl glutamide, dibutylethylhaxanoyl glutamide) by the company Kokyu Alcohol Kogyo.

It is also possible to use silicone waxes, which may advantageously be substituted polysiloxanes, preferably at a low melting point.

Among the commercial silicone waxes of this type, mention may be made, in particular, of those sold under the names Abilwax 9800, 9801 or 9810 (GOLDSCHMIDT), KF910 and KF7002 (SHIN ETSU), or 176-1118-3 and 176-11481 (GENERAL ELECTRIC).

The silicone waxes that may be used may also be alkyl or alkoxydimethicones such as the following commercial products: Abilwax 2428, 2434 and 2440 (GOLDSCHMIDT), or VP 1622 and VP 1621 (WACKER), as well as ($C_{20}$-$C_{60}$) alkyldimethicones, in particular especially the ($C_{30}$-$C_{45}$) alkyldimethicones such as the silicone wax sold under the name SF-1642 by the company GE-Bayer Silicones.

It is also possible to use hydrocarbon waxes modified with silicone or fluorinated groups such as, for example, siliconyl candelilla, siliconyl beeswax and Fluorobeeswax by Koster Keunen.

The waxes may also be chosen from fluorinated waxes.

Butter(s) or Pasty Fatty Substance

For the purposes of the present invention, the term "butter" (also referred to as "pasty fatty substance") is understood to mean a lipophilic fatty compound with a reversible solid/liquid state change and comprising at the temperature of 25° C., a liquid fraction and a solid fraction, and at atmospheric pressure (760 mmHg). In other words, the starting melting temperature of the pasty compound may be less than 25° C. The liquid fraction of the pasty compound measured at 25° C. may represent from 9% to 97% by weight of the compound. This liquid fraction at 25° C. is preferably between 15% and 85%, more preferably between 40% and 85% by weight. Preferably, the one or more butters have an end-of-melting temperature of less than 60° C. Preferably, the butter(s) has/have a hardness less than or equal to 6 MPa.

Preferably, the butters or pasty fatty substances have in the solid state an anisotropic crystalline organization, visible by X-ray observations.

For the purposes of the invention, the melting temperature corresponds to the temperature of the endothermic peak observed in thermal analysis (DSC) as described in ISO 11357-3; 1999. The melting point of a paste or a wax may be measured using a differential scanning calorimeter (DSC), for example the calorimeter sold under the name "DSC 02000" by the company TA Instruments.

Concerning the measurement of the melting temperature and the determination of the end-of-melting temperature, the sample preparation and measurement protocols are as follows: A sample of 5 mg of pasty fatty substance (or butter) or wax previously heated at 80° C. and sampled with magnetic stirring using an equally heated spatula is placed in an airtight aluminum capsule or crucible. Two tests are carried out to ensure the reproducibility of the results.

The measurements are made on the calorimeter mentioned above. The oven is subjected to a nitrogen sweep. Cooling is ensured by the RCS heat exchanger 90. The sample is then subjected to the following protocol, first being brought to a temperature of 20° C. and then subjected to a first temperature rise ranging from 20° C. to 80° C., at the heating rate of 5° C./minute, then cooled from 80° C. to −80° C. at a cooling rate of 5° C./minute and finally subjected to a second temperature rise from −80° C. to 80° C. at a heating rate of 5° C./minute. During the second temperature rise, the variation of the power difference absorbed by the empty crucible and the crucible containing the butter sample is measured as a function of the temperature. The melting point of the compound is the value of the temperature corresponding to the tip of the peak of the curve representing the variation of the difference in power absorbed as a function of temperature. The end-of-melting temperature corresponds to the temperature at which 95% of the sample has melted.

The liquid fraction by weight of the butter (or pasty fatty substance) at 25° C. is equal to the ratio of the enthalpy of fusion consumed at 25° C. with the melting enthalpy of the butter. The enthalpy of melting of the butter or pasty compound is the enthalpy consumed by the compound to pass from the solid state to the liquid state.

The butter is said to be in the solid state when the entirety of its mass is in crystalline solid form. The butter is said to be in the liquid state when the entirety of its mass is in liquid form. The melting enthalpy of the butter is equal to the integral of the whole of the melting curve obtained with the aid of the calorimeter mentioned, with a rise in temperature of 5° C. or 10° C. per minute, according to the standard ISO 11357-3: 1999. The melting enthalpy of the butter is the amount of energy required to pass the compound from the solid state to the liquid state. It is expressed in J/g.

The enthalpy of melting consumed at 25° C. is the amount of energy absorbed by the sample to change from the solid state to the state it exhibits at 25° C. consisting of a liquid fraction and a solid fraction. The liquid fraction of the butter measured at 32° C. preferably represents from 30% to 100% by weight of the compound, preferably from 50% to 100%, more preferably from 60% to 100% by weight of the compound. When the liquid fraction of the butter measured at 32° C. is 100%, the temperature at the end of the melting range of the pasty compound is less than or equal to 32° C. The liquid fraction of the butter measured at 32° C. is equal to the ratio of the enthalpy of melting consumed at 32° C. with the enthalpy of melting of the butter. The enthalpy of melting consumed at 32° C. is calculated in the same way as the enthalpy of melting consumed at 23° C.

As regards the measurement of the hardness, the sample preparation and measurement protocols are as follows: the composition according to the invention or the butter is placed in a mold 75 mm in diameter which is filled to about 75% of its height. In order to overcome the thermal past and control the crystallization, the mold is placed in the Vötsch VC0018 programmable oven where it is first heated to 80° C. for 60 minutes, then cooled from 80° C. to 0° C. at a cooling rate of 5° C./minute, then left at the stabilized temperature of 0° C. for 60 minutes, then subjected to a temperature rise from 0° C. to 20° C., at a rate of heat of 5° C./minute, then left at the stabilized temperature of 20° C. for 180 minutes. The compression force measurement is performed with Swantech's TA/TX2i texturometer. The spindle used is chosen according to the texture: —steel cylindrical spindle 2 mm in diameter for very rigid raw materials; —steel cylindrical spindle 12 mm in diameter for rigid raw materials. The measurement comprises 3 steps: a first step after automatic detection of the surface of the sample where the spindle moves at the measuring speed of 0.1 mm/s, and enters the composition according to the invention, or the butter, to a penetration depth of 0.3 mm, wherein the software records the value of the maximum force reached; a second so-called relaxation stage wherein the spindle stays at this position for one second and wherein the force is noted after 1 second of relaxation; finally a third so-called withdrawal step wherein the spindle returns to its initial position at a speed of 1 mm/s and the energy of withdrawal of the probe (negative force) is noted.

The value of the hardness measured in the first step corresponds to the maximum compression force measured in Newton divided by the surface area of the texturometer cylinder expressed in $mm^2$ in contact with the butter or the composition according to the invention. The value of hardness obtained is expressed in mega-pascals or MPa.

The pasty fatty substance or butter may be chosen from synthetic compounds and compounds of plant origin. A pasty fatty substance may be obtained synthetically from starting materials of plant origin.

The pasty fatty substance is advantageously chosen from:
lanolin and its derivatives such as lanolin alcohol, oxyethylenated lanolines, acetylated lanolin, lanolin esters such as isopropyl lanolate, oxypropylenated lanolines,
polymeric or non-polymeric silicone compounds, such as polydimethylsiloxanes of high molecular weight, polydimethylsiloxanes with side chains of the alkyl or alkoxy type having from 8 to 24 carbon atoms, especially stearyl dimethicones,
polymeric or non-polymeric fluorinated compounds,
vinyl polymers, in particular
homopolymers of olefins,
olefin copolymers,
homopolymers and copolymers of hydrogenated dienes,
linear or branched oligomers, homo or copolymers of alkyl (meth)acrylates preferably having a $C_8$-$C_{30}$ alkyl group,
homo and copolymeric oligomers of vinyl esters having $C_8$-$C_{30}$ alkyl groups,
homo and copolymer oligomers of vinyl ethers having $C_8$-$C_{30}$ alkyl groups,
liposoluble polyethers resulting from the polyetherification between one or more $C_2$-$C_{100}$ and preferably $C_2$-$C_{50}$ diols,
esters and polyesters, and
their mixtures.

According to a preferred embodiment of the invention, the particular butter(s) is/are of vegetable origin such as those described in Ullmann's Encyclopedia of Industrial Chemistry ("Fats and Fatty Oils", A. Thomas, published on 15 Jun. 2000, D01 13.2.2.2 Shea Butter, Borneo Tallow, and Related Fats (Vegetable Butters).

Also may be mentioned more particularly triglycerides $C_{10}$-$C_{18}$ (INCI name: C10-018 Triglycerides) comprising at a temperature of 25° C. and at atmospheric pressure (760 mm Hg) a liquid fraction and a solid fraction, shea butter, Shea Nilotica butter (*Butyrospermum parkii*), Galam butter (*Butyrospermum parkii*), butter or Borneo fat or tengkawang tallow (*Shorea stenoptera*), Shorea butter, Illipé butter, Madhuca butter or Bassia Madhuca *longifolia*, mowrah butter (*Madhuca Latifolia*), Katiau butter (*Madhuca motleyana*), Phulwara butter (*M. butyracea*), mango butter (*Mangifera indica*), Murumuru butter (*Astrocatyum murumuru*), Kokum butter (*Garcinia Indica*), Ucuuba butter (*Virola sebifera*), Tucuma butter, Painya butter (Kpangnan) (*Pentadesma butyracea*), Coffee butter (*Coffea arabica*), Apricot butter (*Prunus Armeniaca*), Macadamia butter (*Macadamia Temifolia*), grape seed butter (*Vitis vinifera*), avocado butter (*Persea gratissima*), olive butter (*Olea europaea*), sweet almond butter (*Prunus amygdalus dulcis*), cocoa butter (*Theobroma cacao*) and sunflower butter, butter under the INCI name *Astrocaryum Murumuru* Seed Butter, butter under the INCI name *Theobroma Grandiflorum* Seed Butter, and butter under the INCI name *Irvingia Gabonensis* Kernel Butter, jojoba esters (blend of wax and hydrogenated jojoban oil) (INCI name: Jojoba esters) and ethyl esters of shea butter (INCI name: Shea butter ethyl esters), and mixtures thereof.

According to a preferred embodiment, a gelling agent for drops (G2), or even drops (G1), according to the invention is a heat-sensitive gelling agent, namely one which reacts with heat, and, in particular, is a gelling agent that is solid at ambient temperature and liquid at a temperature above 35° C., preferably above 40° C., or even above 50° C.

Preferably, the gelling agent is chosen from dextrin palmitates.

According to another preferred embodiment, a gelling agent is a thixotropic gelling agent or capable of conferring a thixotropic behavior on the solution which comprises it. This embodiment is advantageous in that the drops (G2) according to the invention are advantageously obtained by implementing a microfluidic process at ambient temperature. Thus, the gelling agent is preferably chosen from the optionally hydrophobic fumed silica surface.

According to a particular embodiment, a composition according to the invention, in particular the oil phase of the drops (G2), does not comprise an elastomer gel comprising at least one dimethicone, in particular such as marketed by the company NuSil Technology under the name CareSil™ CXG-1104 (INCI: Dimethicone (and) Dimethicone/Vinyl Dimethicone Crosspolymer).

Advantageously, when the oil phase of the drops (G2) comprises at least one gelling agent as described above, in particular chosen from dextrin esters and fatty acid(s), and preferably from the group consisting of palmitates dextrin, dextrin myristates, dextrin palmitates/ethylhexanoates, and mixtures thereof, the oil phase of the drops (G2) further comprises at least one oil having a refractive index close to that of the gelling agent(s), namely an oil having a refractive index, at ambient temperature (25° C.) and atmospheric pressure, of between 1.2 and 1.8, preferably between 1.3 and 1.7, in particular between 1.4 and 1.6, and more preferably between 1.45 and 1.55.

This embodiment is advantageous in that it makes it possible to improve the transparency of the oil phase of the drops (G2), and therefore the transparency of the composition according to the invention.

Advantageously, the oil having a refractive index of between 1.2 and 1.8 is a silicone oil, in particular a phenyl silicone oil.

As silicone oils of the invention, mention may be made, for example, of volatile or non-volatile polymethylsiloxanes (PDMSs) with a linear or cyclic silicone chain, and which are liquid or pasty at ambient temperature, in particular cyclopolydimethylsiloxanes (cyclomethicones) such as cyclohexasiloxane and cyclopentasiloxane; polydimethylsiloxanes (or dimethicones) comprising alkyl, alkoxy or phenyl groups, within or at the end of the silicone chain, groups having from 2 to 24 carbon atoms; phenyl silicones such as phenyltrimethicones (in particular diphenylsiloxyphenyltrimethicone), phenyldimethicones, phenyltrimethylsiloxydiphenylsiloxanes, diphenyl-dimethicones, diphenylmethyldiphenyltrisiloxanes, 2-phenylethyltrimethylsiloxysilicates and polymethylphenylsiloxanes, and mixtures thereof.

According to one embodiment, a composition according to the invention comprises from 0.1% to 75%, preferably from 0.2% to 60%, in particular from 0.5% to 40%, better still from 0.7% to 20%, and preferably from 1% to 4%, by weight of gelling agent(s) relative to the total weight of the composition.

According to the invention, a composition according to the invention may comprise from 0.5% to 98.99%, preferably from 1% to 70%, in particular from 1.5% to 50%, better still from 2% to 40% by weight, in particular from 2.5% to 30%, and preferably from 10% to 20%, by weight of gelling agent(s) relative to the total weight of the oil phase of the drops (G2), or even drops (G1) and (G2).

Preferably, a composition according to the invention comprises more than 10%, preferably more than 15%, and more preferably more than 20%, by weight of oil phase relative to the total weight of said composition.

Continuous Aqueous Phase

In addition to the anionic polymers (PA1) and (PA2) as defined above, the aqueous phase of the compositions according to the invention comprises water, preferably in the form of a gel.

In addition to distilled or deionized water, water suitable for the invention may also be natural spring water or floral water.

According to one embodiment, the mass percentage of water of the aqueous continuous phase of a composition according to the invention is at least 40%, and better still at least 50%, especially between 70% and 98%, preferably between 75% and 95%, relative to the total mass of the continuous phase.

The compositions according to the invention may comprise at least 20%, preferably at least 30%, in particular at least 40%, and better still at least 50% by weight of water relative to the total weight of the composition.

Preferably, the compositions according to the invention comprise at least 75% by weight of aqueous phase.

The continuous aqueous phase of a composition according to the invention may further comprise at least one base. It may comprise a single base or a mixture of several different bases. The presence of at least one base in the aqueous continuous phase contributes, in particular, to enhancing the viscosity of the latter.

According to one embodiment, the base present in the aqueous phase is a mineral base.

According to one embodiment, the mineral base is selected from the group consisting of alkali metal hydroxides and alkaline earth metal hydroxides.

Preferably, the mineral base is an alkali metal hydroxide, and especially NaOH.

According to one embodiment, the base present in the continuous aqueous phase is an organic base. Among the organic bases, mention may be made, for example, of ammonia, pyridine, triethanolamine, aminomethylpropanol, or else triethylamine.

A composition according to the invention may comprise from 0.01% to 10% by weight, preferably from 0.01% to 5% by weight, more preferably from 0.02% to 1% by weight of base, preferably a mineral base, and especially NaOH, relative to the total weight of the composition.

Shell of the Drops

As mentioned above, the drops (G1) and (G2) according to the invention are surrounded by a shell (also referred to as a "membrane").

According to the invention, the drops obtained may have a very thin shell, in particular with a thickness less than 1% of the diameter of the drops (G1) and (G2).

The thickness of the shell is thus preferably less than 1 μm and is too small to be measured by optical methods.

According to one embodiment, the thickness of the shell of the drops (G1) and (G2) is less than 1000 nm, in particular between 1 and 500 nm, preferably less than 100 nm, advantageously less than 50 nm, more preferably less than 10 nm.

The measurement of the thickness of the shell of the drops of the invention may be carried out by the Small-Angle X-ray Scattering method, as implemented in Sato et al. J. Chem. Phys. 111, 1393-1401 (2007).

For this purpose, the drops are produced using deuterated water and are then washed three times with a deuterated oil, such as, for example, a deuterated hydrocarbon-type oil (octane, dodecane, hexadecane).

After washing, the drops are then transferred to the Neutron cell to determine the I(q) spectrum; wherein q is the wave vector.

From this spectrum, conventional analytical treatments (REF) are applied to determine the thickness of the hydrogenated (undeuterated) shell.

According to one embodiment, the shell surrounding the drops of the dispersed phase is stiffened, which in particular gives good resistance to the drops and reduces or even prevents their coalescence.

This shell is typically formed by coacervation, i.e. precipitation of charged polymers of opposite charges. Within a coacervate, the bonds binding the charged polymers to each other are of ionic type, or even of hydrogen and hydrophobic type, and are generally stronger than bonds present within a membrane of the surfactant type.

The shell is formed by coacervation of at least two charged polymers of opposite polarity (or polyelectrolyte) and preferably in the presence of a first polymer, of cationic type, and a second polymer, different from the first polymer, of the anionic type. These two polymers act as stabilizing agents, or even stiffening, of the membrane.

The formation of the coacervate between these two polymers is generally caused by a modification of the conditions of the reaction medium (temperature, pH, reagent concentration, etc.). The coacervation reaction results from the neutralization of these two charged polymers of opposite polarities and allows the formation of a membrane structure by electrostatic interactions between the anionic polymer and the cationic polymer. The membrane thus formed around each drop typically forms a shell which completely encapsulates the core of the drop and thus isolates the core of the drop from the continuous aqueous phase.

Anionic Polymers

As indicated above, the drops (G1) and (G2) comprise shells formed from at least one anionic polymer (PA1) or (PA2) respectively.

According to the invention, the anionic polymers (PA1) and (PA2) are identical or different.

The anionic polymers (PA1) and (PA2) are used for the formation, respectively, of the shell of the drops (G1) and (G2). The anionic polymer (PA1), or even (PA2), also contributes to increasing the viscosity of the aqueous continuous phase of a composition according to the invention.

In the context of the present description, the term "anionic polymer" (or "anionic type polymer") is understood to mean a polymer having chemical functions of anionic type. We can also speak of anionic polyelectrolyte.

"Anionic chemical function" is understood to mean a chemical function AH capable of giving a proton to give a function A$^-$. Depending on the conditions of the medium in which it is found, the anionic type polymer therefore has chemical functions in AH form, or in the form of its conjugate base A$^-$.

As an example of chemical functions of the anionic type, mention may be made of the carboxylic acid functions —COOH, optionally present in the form of carboxylate anion —COO$^-$.

As an example of anionic type polymer, mention may be made of any polymer formed by the polymerization of monomers, at least a part of which carries anionic type chemical functions, such as carboxylic acid functions. Such monomers are, for example, acrylic acid, maleic acid, or any ethylenically unsaturated monomer containing at least one carboxylic acid function.

Preferably, the anionic polymer is hydrophilic, i.e. soluble or dispersible in water. In the context of the invention, and unless otherwise stated, the term "hydrophilic" is understood to mean the property according to which a given body is compatible with water or a polar solvent, i.e. it can accept water. water or the solvent, to form with them a homogeneous phase, for example a solution.

According to the invention, the anionic polymers (PA1) and (PA2) are identical or different.

According to one embodiment, the anionic polymers (PA1) and (PA2), which are identical or different, are polymers comprising monomeric units comprising at least one carboxylic acid function.

Examples of suitable anionic polymers for carrying out the invention include copolymers of acrylic acid or maleic acid and other monomers, such as acrylamide, alkyl acrylates, $C_5$-$C_8$ alkyl acrylates, $C_{10}$-$C_{30}$ alkyl acrylates, $C_{12}$-$C_{22}$ alkyl methacrylates, methoxy-polyethylene glycol methacrylates, hydroxyester acrylates, crosspolymer acrylates, and mixtures thereof.

Preferably, the anionic polymers (PA1) and (PA2), which are identical or different, are chosen from carbomers and crosslinked acrylate/$C_{10\text{-}30}$ alkyl acrylate copolymers. Preferably, the anionic polymers (PA1) and (PA2) according to the invention are carbomers, which are identical or different.

In the context of the invention, and unless otherwise stated, the term "carbomer" is understood to mean an optionally crosslinked homopolymer resulting from the polymerization of acrylic acid. It is therefore a poly(acrylic acid) optionally crosslinked.

Among the carbomers of the invention, mention may be made of those sold under the names Tego®Carbomer 340FD from Evonik, Carbopol® 981 from Lubrizol, Carbopol ETD 2050 from Lubrizol or Carbopol Ultrez 10 from Lubrizol.

According to one embodiment, the term "carbomer" or "carbomer" or "Carbopol®" is understood to mean a high molecular weight acrylic acid polymer crosslinked with allyl sucrose or pentaerythritol allyl ethers (handbook of Pharmaceutical Excipients, 5th Edition, pill). Examples include Carbopol®10, Carbopol®934, Carbopol®934 P, Carbopol®940, Carbopol®941, Carbopol®71 G, Carbopol®980, Carbopol®971 P, or Carbopol®974 P. According to one embodiment, the viscosity of the carbomer is between 4,000 and 60,000 cP at 0.5% w/w at a pH of between 4.5 and 7.0.

The carbomers have other names: polyacrylic acids, carboxyvinyl polymers or carboxy polyethylenes.

According to the invention, the above-mentioned composition may comprise from 0.01% to 10%, preferably from 0.05% to 5%, in particular from 0.1% to 3%, by weight of anionic polymer(s), especially carbomer(s), relative to the total weight of the composition.

According to the invention, the anionic polymers (PA1) and (PA2) may also be a crosslinked copolymer acrylates/$C_{10-30}$ alkyl acrylate (INCI name: acrylates/$C_{10-30}$ alkyl acrylate crosspolymer) as defined above.

According to the invention, the compositions according to the invention may comprise a carbomer and a crosslinked copolymer acrylates/$C_{10-30}$ alkyl acrylate.

Cationic Polymers

As indicated above, the drops (G1) and (G2) comprise shells formed of at least one cationic polymer (PC1) or (PC2) respectively.

According to the invention, the cationic polymers (PC1) and (PC2) are identical or different.

The drops (G1) or (G2) may also comprise several cationic type polymers.

In the context of the present application, and unless otherwise stated, the term "cationic polymer" (or "cationic type polymer") is understood to mean a polymer having chemical functions of cationic type. We can also speak of cationic polyelectrolyte.

Preferably, the cationic polymer(s) is/are lipophilic or liposoluble.

In the context of the present application, and unless otherwise stated, "chemical function of cationic type" is understood to mean a chemical function B capable of capturing a proton to give a function BH$^+$. Depending on the conditions of the medium in which it is located, the cationic type polymer therefore has chemical functions in B form, or in BH$^+$ form, its conjugated acid.

As an example of chemical functions of cationic type, mention may be made of the primary, secondary and tertiary amine functions, optionally present in the form of ammonium cations.

As examples of cationic polymers, mention may be made of any polymer formed by the polymerization of monomers at least a part of which carries chemical functions of cationic type, such as primary, secondary or tertiary amine functions.

Such monomers are, for example, aziridine, or any ethylenically unsaturated monomer containing at least one primary, secondary or tertiary amine function.

Examples of cationic polymers suitable for the implementation of the invention include amodimethicone, derived from a silicone polymer (polydimethylsiloxane, also called dimethicone), modified by primary amine functions and secondary amine.

Mention may also be made of amodimethicone derivatives, for example copolymers of amodimethicone, amino-propyl dimethicone, and, more generally, linear or branched silicone polymers containing amine functional groups.

Bis-isobutyl PEG-14/amodimethicone copolymer, bis ($C_{13}$-$C_{15}$ alkoxy) PG-amodimethicone, bis-cetearyl amodimethicone and bis-hydroxy/methoxy amodimethicone may also be mentioned.

Mention may also be made of polysaccharide polymers comprising amine functions, such as chitosan or guar gum derivatives (hydroxypropyltrimonium guar chloride).

Mention may also be made of polypeptide polymers comprising amine functions, such as polylysine.

Mention may also be made of polyethyleneimine polymers comprising amine functions, such as linear or branched polyethyleneimine.

According to one embodiment, the drops (G1) or (G2), and, in particular, the shell of the drops, comprise a cationic polymer (PC1), or (PC2) respectively, which is a silicone polymer modified with a primary amine, secondary or tertiary function, such as amodimethicone.

According to one embodiment, the drops (G1) or (G2), and, in particular, the shell of the drops, comprise amodimethicone.

According to a particularly preferred embodiment, the cationic polymer has the following formula:

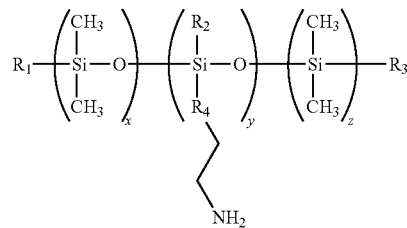

in which:

$R_1$, $R_2$ and $R_3$, independently of each other, represent OH or $CH_3$;

$R_4$ represents a group —$CH_2$— or a group —X—NH— in which X is a divalent alkylene radical $C_3$ or $C_4$;

x is an integer between 10 and 5000, preferably between 30 and 1000, and more preferably between 80 and 300;

y is an integer between 2 and 1000, preferably between 4 and 100, and more preferably between 5 and 20; and z is an integer between 0 and 10, preferably between 0 and 1, and even better equal to 1.

In the aforementioned formula, when $R_4$ is —X—NH—, X is attached to the silicon atom.

In the aforementioned formula, $R_1$, $R_2$ and $R_3$ are preferably $CH_3$.

In the aforementioned formula, $R_4$ is preferably a —($CH_2$)$_3$—NH— group.

According to the invention, the drops (G1) and (G2) may comprise from 0.01% to 10%, preferably from 0.05% to 5%, in particular from 0.1 to 3%, by weight of cationic polymer(s) (PC1) and (PC2), in particular amodimethicone(s), relative to the total weight of the oil phase of the drops (G1) and (G2).

Additional Compound(s)/Active Agent(s)

A composition according to the invention may further comprise at least one additional compound other than the anionic and cationic polymers, gelling agents and oils mentioned above, preferably chosen from powders, flakes and coloring agents, chosen in particular from coloring agents, whether water-soluble or not, liposoluble or not, organic or inorganic, optical effect materials, liquid crystals, particulate agents, emulsifying and/or non-emulsifying silicone elastomers, especially as described in EP2353577, preservatives, humectants, stabilizers, chelators, texturizing agents, emollients, etc. or any usual cosmetic additive, and mixtures thereof.

In particular, a composition according to the invention may further comprise, as additional compound(s), at least one adjuvant, such as at least one compound chosen from fillers, and in particular soft-focus effect powders, mattifying powders, which may be chosen, in particular, from polyamides, silica, talc, mica, fibers (in particular of polyamide or of cellulose); nylon-6, methyl methacrylate crosspolymer, and mixtures thereof.

Such additional compounds may be located in the continuous aqueous phase of a composition according to the invention, in the drops (G1) and/or in the drops (G2).

In particular, a composition according to the invention, preferably drops (G2), comprises at least one coloring agent. The presence of such a coloring agent makes it possible to have cosmetic products with an enhanced visual attractiveness.

A coloring agent that can be used in the context of the present invention is, in particular, as described in application FR1558848.

In particular, a composition according to the invention, preferably the aqueous continuous phase, comprises at least one texturing agent. The presence of such a texturing agent makes it possible to vary the fluidity and/or the sensoriality of the composition. A texturing agent, particularly hydrophilic, i.e. soluble or dispersible in water, that may be used in the context of the present invention, is, in particular, described in the application FR1558849.

Preferably, the texturizing agents of the aqueous phase are chosen from among those which are resistant to electrolytes and may be used over a wide pH range, and are, in particular, chosen from methylcellulose; ethylcellulose; the AMPS Na/hydroxyethyl acrylate copolymers sold under the names Sepinov WEP or Sepinov EMT 10; acryloyl Dimethyltaurate/Sodium Acrylate/Dimethylacrylamide crosspolymers; polyacrylate crosspolymer-6; polyurethane-39; cetyl hydroxyethylcellulose; glycerine; the carbomers represented by those sold under the names Carbopol Ultrez 10/30, and acrylate copolymers, in particular those marketed under the names Carbopol Aqua SF-1 Polymer or Carbopol Aqua SF-1 OS Polymer; sodium acrylates/beheneth-25 methacrylate crosspolymer; acrylates/acrylamide copolymers; alcasealan (INCI: Alcaligenes Polysaccharides); and mixtures thereof, and more preferably selected from acrylate copolymers, in particular the product sold under the name Carbopol Aqua SF-1 Polymer.

These texturing agents, in addition to their property of resistance to electrolytes and/or stability over a wide pH range (in particular pH between 4.5 and 7.0), give a composition according to the invention comprising improved stability and transparency.

Furthermore, a composition according to the invention may comprise at least one additional active agent, preferably chosen from hydrating agents, cicatrizing agents, depigmenting agents, UV-screening agents, desquamating agents, antioxidant agents, and synthesis stimulating agents. dermal and/or epidermal macromolecular agents, derembodiment-contracting agents, antiperspirants, soothing agents, anti-aging agents, perfuming agents and mixtures thereof. Such active agents are, in particular, described in FR 1 558 849.

As representative of active agents that may be used in the present invention, mention may be made more particularly of adenosine, retinol and its derivatives, ascorbic acid and its derivatives, such as ascorbyl glucoside; tocopherol and its derivatives, such as tocopheryl acetate; nicotinic acid and its precursors, such as nicotinamide, plant extracts and especially rye seed extracts under the trade name Coheliss de Silab; an extract of leaves of *Centella asiatica*; oily or aqueous extracts of flowers and/or leaves of *Camellia japonica*; plant cells, licorice extract (*Glycyrrhiza glabra*), *zingiber* root extract, glycerin; diglycerin; glycols, such as sorbitol; betaines; urea and its derivatives, α-hydroxy acids; β-hydroxy acids, such as salicylic acid, lipopeptides sold by SEDERMA under the trade names Biopeptide CL, Matrixyl 500 and Matrixyl 3000, homopolymers and co-polymers of 2-methacryloyloxy-ethylphosphorylcholine acid, such as Lipidure HM and PBM lipid NOF, glycosaminoglycans and derivatives thereof such as hyaluronic acid, sodium hyaluronate and acetylated hyaluronic acid, free amino acids and their derivatives; glucosamine; citric acid; ceramides; and their mixtures.

The compositions may further comprise at least one compound rich in polyunsaturated fatty acids other than an oil (H2) as described above and, in particular, chosen from an extract of microalgae (for example *spirulina* (*Spirulina maxima* and *Spirulina platensis*), a zooplankton extract, a fish oil; and their mixtures.

Such additional active agents may be located in the continuous aqueous phase of a composition according to the invention, in the drops (G1) and/or in the drops (G2).

In particular, a composition according to the invention, preferably drops (G1), comprises at least one perfuming agent.

Of course, those skilled in the art will take care to choose any additional compound(s) and/or active agent(s) and/or their quantity in such a way that the advantageous properties of a composition according to the invention, in particular the integrity of the drops (G1) and (G2), are not, or not substantially, impaired by the addition envisaged. Furthermore, the nature and/or the amount of any additional compound(s) and/or active agent(s) depends on the aqueous or fatty nature of the phase considered of the composition according to the invention. These adjustments are within the expertise of those skilled in the art.

According to one embodiment, the compositions according to the invention contain less than 2%, or even less than 1%, preferably less than 0.5%, by weight of compounds having surface-active properties.

Preferably, the compositions according to the invention do not comprise a surfactant.

Thus, the low content, and even the absence, of surfactants will advantageously block the phenomenon of compositional maturation of the drops (G2) towards the drops (G1), which makes it possible to guarantee the maintenance of the integrity and properties of the drops (G2), and therefore the advantageous properties of a composition according to the invention described above.

In view of the above, the dispersed oil phase of a composition according to the invention may further comprise gelled drops (G3), or even gelled drops (G4), (G5), etc., but that are different from the gelled drops (G2).

These differences may be achieved in terms of diameter and/or color and/or cationic polymer and/or anionic polymer and/or gelling agent and/or compound(s) and/or additional active agent(s) implemented for the preparation of gelled drops (G2) and (G3), or even gelled drops (G4), (G5), etc.

The present invention also relates to the use of an oil-in-water emulsion comprising a continuous aqueous phase and a dispersed oil phase in the form of drops (G1) as defined above, to improve the stability and/or preserve the drop (G2) integrity as defined above.

Preparation Procedure

A composition according to the invention may be prepared, in particular, via the two procedures described hereinafter, designated respectively procedure No. 1 and procedure No. 2.

Procedure No. 1

According to a first embodiment, the present invention relates to a procedure for preparing a composition as defined above, comprising the following steps:

a) the preparation of an oil-in-water emulsion (E1) comprising drops (G1), by stirring an oil phase in an aqueous phase, wherein the oil phase comprises at least one cationic polymer (PC1) and in addition, optionally, at least one additional active agent and/or compound as mentioned above, and wherein the aqueous phase comprises at least water and at least one anionic polymer (PA1) and additionally, optionally, at least one additional active agent and/or compound as mentioned above, or even a base, preservatives and/or other water-soluble products such as glycerine, b) the preparation of an oil-in-water emulsion (E2) comprising an aqueous phase, which is identical to or different from the aqueous phase of the emulsion (E1), and drops (G2), by bringing into contact an oily fluid FI, wherein the oily fluid FI comprises at least one cationic polymer (PC2), identical to or different from (PC1), and optionally at least one gelling agent, and an aqueous fluid FE, wherein the aqueous fluid FE comprises at least water and at least one anionic polymer (PA2), identical or different from (PA1), to form drops (G2), preferably monodisperse, comprising an oil phase, consisting of the oily fluid FI, dispersed in a continuous aqueous phase, consisting of FE fluid, wherein the drops (G2) comprise a shell insulating the core of the drops of the oil phase, c) the mixing of the emulsions (E1) and (E2), and d) optionally, adding a solution to increase the viscosity of the aqueous phases, preferably comprising a base, in particular an alkaline hydroxide, such as sodium hydroxide, and/or a solution comprising at least one texturizing agent for the aqueous phases, in particular as described above, to vary their fluidity and/or sensoriality and therefore the fluidity and/or the sensoriality of the composition according to the invention.

Step b) relating to the preparation of the emulsion (E2), especially when the fluid F1 comprises at least one gelling agent, wherein, in particular, a heat-sensitive agent, may consist of:

heating an oily fluid F1 to a temperature of between 35° C. and 150° C., wherein the oily fluid F1 comprises at least one cationic polymer (PC2) identical to or different from (PC1), and optionally at least one gelling agent and in addition, optionally, at least one additional compound and/or active agent as mentioned above; and contacting the oily fluid F1 and an aqueous fluid FE, wherein the aqueous fluid FE comprises at least water and at least one anionic polymer (PA2), identical or different from (PA1), and additionally, optionally, at least one additional active agent and/or compound as mentioned above or a base, preservatives and/or other water-soluble products such as glycerine, to form drops (G2), preferably monodisperse, comprising an oil phase, consisting of the oily fluid FI, dispersed in a continuous aqueous phase, consisting of FE fluid, wherein the drops (G2) comprise a shell insulating the core of the drops of the oil phase.

The temperature of the heating step of the aforementioned fluid F1 is adapted, in particular, to the quantity and/or the nature of the gelling agent used, in particular so that it is in liquid form. This adaptation is within the expertise of those skilled in the art.

In this procedure, steps a) and b) may be performed in the order a) and then b), b) and a), or even in parallel.

This first embodiment, therefore, consists in separately preparing each of the emulsions (E1) and (E2) and then mixing them to obtain the composition according to the invention.

According to this first embodiment, the method may furthermore comprise a step e), prior to step c) but subsequent to step b), consisting in carrying out a partial or total filtration of the emulsion (E2) to remove all or part of the continuous aqueous phase (i.e. the aqueous fluid FE) and recover a more or less concentrated solution in drops (G2). This optional step then makes it possible to control the drop content (G2) in the final composition.

Those skilled in the art will be able to adjust the parameters and/or materials required to achieve the desired drop content (G2).

According to the invention, this filtration step e) may be carried out by mechanical filtration, strainer-sieve, suction of the aqueous phase continuously, or after creaming of the drops (G2).

Preparation of the Emulsion (E1) with Procedure No. 1

According to a first variant embodiment, the aforementioned emulsion (E1) is prepared according to a simple "non-microfluidic" method, namely by simple emulsification. As in a conventional emulsion, an aqueous solution and an oily solution are prepared separately. It is the stirring addition of the oil phase in the aqueous phase which creates the direct emulsion.

According to another variant embodiment, the above-mentioned emulsion (E1) is prepared according to a "microfluidic" method, in particular as described in the applications WO2012/120043 or WO2015/055748 or the application FR1558850.

Preparation of the Emulsion (E2) with Procedure No. 1

The emulsion (E2) may be prepared according to a microfluidic process, in particular as described in the applications WO2012/120043 or WO2015/055748 or the application FR1558850. In other words, the emulsion (E2) is advantageously not prepared according to a "non-microfluidic" process, namely by simple emulsification.

It is this microfluidic process that makes it possible to give the drops (G2) the properties of uniform size and monodispersity previously described.

As indicated above, the solutions (or fluids) used to constitute the continuous aqueous phase and the dispersed oil phase of this emulsion (E2) are respectively designated External Fluid (FE) and Internal Fluid (FI).

In view of the above, the procedure for preparing the emulsion (E2) according to the invention may comprise a step of heating the oily fluid FI, comprising the oil phase of the emulsion (E2), at a temperature of 40° C. and 150° C., preferably 50° C. to 90° C., prior to the aforementioned step of forming the drops (G2), and therefore before mixing/contacting the oil phase with the aqueous phase.

According to one embodiment, the temperature of the heating step is from 50° C. to 80° C.

Advantageously, the presence of a gelling agent in the oily fluid FI makes it possible to dispense with the use of an intermediate fluid as described in Application WO2012/120043.

Advantageously, the fluid FE is also heated to a temperature of 35° C. to 150° C., preferably 50° C. to 100° C. during step b).

Procedure 2

According to a second embodiment, the present invention relates to a procedure for preparing a composition as defined above, comprising the following steps:
- a) the preparation of an oil-in-water emulsion (E1) comprising drops (G1), by stirring an oil phase in an aqueous phase, wherein the oil phase comprises at least one cationic polymer (PC1), and additionally, optionally, at least one additional active agent and/or compound as mentioned above, and wherein the aqueous phase comprises at least water and at least one anionic polymer (PA1) and additionally, optionally, at least one additional active agent and/or compound as mentioned above, or even a base, preservatives and/or other water-soluble products such as glycerin,
- b) contacting the emulsion (E1) with an oily fluid F1 comprising at least one cationic polymer (PC2), identical to or different from (PC1), and optionally at least one gelling agent, and the formation of drops (G2) comprising an oil phase, consisting of the oily fluid FI, dispersed in the emulsion (E1); and
- d) optionally, adding a solution to increase the viscosity of the aqueous phase, preferably comprising a base, in particular an alkaline hydroxide, such as sodium hydroxide, and/or a solution comprising at least one texturizing agent, in particular as described above, for varying the fluidity and/or the sensoriality of the aqueous phase and thus of the composition according to the invention.

Step b), especially when the fluid F1 comprises at least one gelling agent, in particular a heat-sensitive agent, may consist of:
- heating an oily fluid F1 to a temperature of between 35° C. and 150° C., wherein the oily fluid F1 comprises at least one cationic polymer (PC2), identical to or different from (PC1), and at least one gelling agent and additionally, optionally, at least one additional active agent and/or compound as mentioned above; and
- contacting the emulsion (E1) and the oily fluid FI, and the formation of the drops (G2) comprising an oil phase, consisting of the oily fluid FI, dispersed in the emulsion (E1).

The temperature of step b) for heating the aforementioned fluid F1 is adapted, in particular, to the quantity and/or the nature of the gelling agent used, in particular so that it is in liquid form. This adaptation is within the expertise of those skilled in the art.

Advantageously, the emulsion (E1) is also heated to a temperature of 35° C. to 150° C., preferably 50° C. to 100° C., during step b).

Preparation of the Emulsion (E1) with Procedure No. 2

The aforementioned emulsion (E1) is prepared according to the same "non-microfluidic" and "microfluidic" methods as described above for procedure No. 1.

Nevertheless, the emulsion (E1) here preferably has a viscosity of less than 3000 cPs as measured at 25° C. and according to the protocol described above and/or is heated to a temperature of between 35° C. and 150° C., preferably from 50° C. to 100° C., during step b).

Preparation of the Composition According to the Invention with Procedure No. 2

This second embodiment differs from the first embodiment above in that an emulsion (E2) is not produced. In fact, with this procedure No. 2, a composition according to the invention is prepared according to a microfluidic process, where appropriate hot, especially as described in the application FR1558850, wherein the emulsion (E1) is used as a continuous phase (or FE fluid) for the manufacture of the drops (G2).

It is this microfluidic process that makes it possible to give the drops (G2) the properties of uniform size and monodispersity previously described.

Advantageously, the presence of a gelling agent in the oily fluid F1 makes it possible to dispense with the use of an intermediate fluid as described in application WO2012/120043.

Advantageously, the temperature of the heating step is from 50° C. to 100° C., preferably from 60° C. to 90° C.

Advantageously, the emulsion (E1) is also heated to a temperature of from 35° C. to 150° C., preferably from 50° C. to 100° C., in particular from 60° C. to 90° C., before producing the aforementioned step b) of contacting the emulsion (E1) and the oily fluid F1.

According to one variant, the emulsion (E1) is devoid of perfuming agent.

According to another variant, the emulsion (E1), in particular the drops (G1), further comprises at least one perfuming agent.

The procedure according to this second embodiment may also comprise, after step b) of forming drops (G2) (and preferably before step d)), a step e) of adding at least one emulsion (E1') oil-in-water comprising drops (G1') comprising at least one heat-sensitive compound, wherein the drops (G1') comprise an oil phase and a shell formed of at least one anionic polymer (PA1') and at least one cationic polymer (PC1'), wherein the size of the drops (G1') is less than 500 μm, or even less than 200 μm. The anionic polymers (PA1') and the cationic polymers (PC1') correspond to the definitions given above for (PA1) and (PC1) respectively.

Such a heat-sensitive compound may, for example, be a perfuming agent, a dye, a cosmetic active agent, and mixtures thereof, preferably a perfuming agent.

Advantageously, this step e) of adding at least one emulsion (E1') is carried out at room temperature, preferably after a return of the composition obtained in step b) to ambient temperature.

According to one embodiment, this step e) of adding at least one emulsion (E1') is carried out by mixing, for example, via a static mixer.

This second embodiment is particularly advantageous in that it constitutes a simplified alternative to the procedure according to the first embodiment above (i.e. procedure No. 1). In fact, the procedure according to this second embodiment makes it possible to dispense with the filtration step d) described above but, above all, leads directly to obtaining a composition according to the invention in which the drops (G2) are homogeneously dispersed. In fact, this procedure No. 2 allows better control of the composition.

In other words, the procedure according to this second embodiment does not require a filtration step or mixing in the manner of steps e) and c) of the procedure according to the first embodiment, and thus prevents any possible deterioration/bursting of the drops (G2).

For the preparation procedures according to the first and second embodiments described above, the procedures may further comprise:

a step of injecting a solution to increase the viscosity of the continuous aqueous phase of the emulsion (E1), or even of the emulsion (E2).

According to one embodiment, the solution for increasing the viscosity comprises a base, in particular an alkaline hydroxide, such as sodium hydroxide.

Preferably, the viscosity-increasing solution is aqueous.

In the procedure according to the first embodiment above, this step of adding a solution to increase the viscosity is carried out simultaneously and/or after the step c) of mixing the emulsions (E1) and (E2), preferably after this step c).

In the procedure according to the second embodiment above, this step of adding a solution to increase the viscosity is carried out after step b) of forming the gelled drops (G2) and, where appropriate, after step e) above.

a step of injecting a solution comprising at least one texturing agent as described above to vary the fluidity and/or the sensoriality of the aqueous phase of the emulsion (E1), or even of the emulsion (E2), and therefore of the composition according to the invention.

Preferably, this solution is aqueous and the texturing agent(s) is/are hydrophilic.

In the procedure according to the first embodiment above, this step is carried out simultaneously and/or after step c) of mixing the emulsions (E1) and (E2), preferably after this step c).

In the procedure according to the second embodiment above, this step is performed after step b) of forming the drops (G2) and, where appropriate, after step e) mentioned above, a step of packaging the composition thus obtained in any suitable packaging device.

Finally, those skilled in the art, in view of the foregoing, will be able to adjust/adapt the preparation procedures described above in the event that the composition according to the invention further comprises drops (G3) or drops (G4), (G5), etc., where appropriate gelled, but different from the drops (G2) as described above.

Uses

In a preferred manner, a composition according to the invention is directly usable, at the end of the aforementioned preparation processes, as a composition, in particular a cosmetic composition.

The compositions according to the invention may, in particular, be used in the cosmetics field.

They may comprise, in addition to the aforementioned ingredients, at least one physiologically-acceptable medium.

"Physiologically-acceptable medium" is understood to mean a medium which is particularly suitable for the application of a composition of the invention to keratin materials, in particular the skin, the lips, the nails, the eyelashes or the eyebrows, and preferably the skin.

The physiologically-acceptable medium is generally adapted to the nature of the support to which the composition is to be applied, as well as to the appearance under which the composition is to be packaged.

According to one embodiment, the cosmetic compositions are used for the make-up and/or care of keratin materials, especially the skin.

The cosmetic compositions according to the invention may be products for care, sun protection, cleaning (make-up removal), hygiene or make-up of the skin.

These compositions are topical and therefore intended to be applied especially to the skin.

Thus, the present invention also relates to the non-therapeutic cosmetic use of a cosmetic composition mentioned above, as a make-up, hygiene, cleaning and/or care product for keratin substances, in particular the skin.

In particular, the present invention relates to the non-therapeutic use of a cosmetic composition according to the invention for the care of a keratin material, in particular the skin, and, in particular, for preventing and/or treating the cutaneous signs of aging, chronological and/or photo-induced, and/or hydrating the keratin material, in particular the skin.

"Cutaneous signs of aging", and in particular "signs of aging of the skin" is understood to mean within the context of the invention, any changes in the external appearance of the skin due to aging, whether chronobiological and/or photo-induced, such as wrinkles and fine lines, wilted skin, soft skin, thinned skin, lack of elasticity and/or tone of the skin, lack of density and/or firmness of the skin, but also any internal changes in the skin that do not systematically result in a modified external appearance, such as any internal damage to the skin resulting from exposure to ultraviolet radiation.

According to one embodiment, the compositions of the invention are in the form of a foundation, a make-up remover, facial and/or body and/or product for hair care, anti-aging, sunscreen, oily skin care, whitening care, moisturizer, or a BB cream, a tinted cream or a foundation, a face and/or body cleanser, shower gel or shampoo.

A care composition according to the invention may be, in particular, a solar composition, a care cream, a serum or a deodorant.

The compositions according to the invention may be in various forms, in particular in the form of cream, balm, lotion, serum, gel, cream gel or mist.

The present invention also relates to a non-therapeutic method for the cosmetic treatment of a keratin material, comprising a step of applying to the keratin material at least one layer of a cosmetic composition as defined above.

In particular, the present invention relates to a non-therapeutic method for cosmetic treatment of the skin, comprising a step of applying to the skin at least one layer of a cosmetic composition as defined above.

Throughout the description, including the claims, the phrase "comprising one" should be understood as being synonymous with "comprising at least one", unless the opposite is specified.

The expressions "comprised between . . . and . . . ", "comprised from . . . to . . . " and "going from . . . to . . . " must be understood as being inclusive, unless otherwise specified.

The amounts of the ingredients in the examples are expressed as percentage by weight relative to the total weight of the composition, unless otherwise indicated.

The examples which follow illustrate the present invention without limiting its scope.

EXAMPLES

Example 1: Surfactants/Gelled Drops (G2) Compatibility

The present study aims to evaluate the compatibility of gelled drops (G2) according to the invention in contact with two surfactants commonly used in the aqueous phases of cosmetic creams.

The drops (G2) considered in this study are stained blue for visualization in surfactant solutions and in creams. These gelled drops (G2) were obtained by means of a hot microfluidic device (about 80° C.) as described in FR1558850 by implementing the aqueous and oil phases described in the table below:

| Name | INCI name | % w/w PHASES | % w/w |
|---|---|---|---|
| AQUEOUS PHASE | | | |
| Osmosis water | Water | 87.59 | 78.84 |
| Microcare PE | Phenoxyethanol | 0.89 | 0.80 |
| Microcare PTG | Pentylenglycol | 2.22 | 2.00 |
| Tego Carbomer 340 FD | Carbomer | 0.22 | 0.20 |
| Glycerine codex (99%) | Glycerin | 9.00 | 8.10 |
| EDETA BD | Disodium EDTA | 0.036 | 0.03 |
| Sodium Hydroxide Pellets PRS codex | Sodium Hydroxide | 0.033 | 0.03 |
| | | 100.00 | 90.00 |
| OILY PHASE | | | |
| DUB ININ | Isononyl Isononanoate | 84.50 | 8.45 |
| Rheopearl KL2 | Dextrin Palmitate | 15.00 | 1.50 |
| Phat Blue DC6204 | CI 61565, CI 60725 | 0.0039 | 0.00039 |
| KF 8004 | Amodimethicone | 0.50 | 0.05 |
| | | 100.00 | 10.00 |

Once the emulsion was made, the gelled drops (G2) were isolated from the aqueous phase by filtration before the tests described below.

The gelled drops (G2) obtained thus have the following composition:

| Drops (G2) | | |
|---|---|---|
| DUB ININ | Isononyl Isononanoate | 84.50 |
| Rheopearl KL2 | Dextrin Palmitate | 15.00 |
| Phat Blue DC6204 | CI 61565, CI 60725 | 0.0039 |
| KF 8004 | Amodimethicone | 0.50 |
| Tego Carbomer 340 FD | Carbomer | * |
| Total | | 100.00 |

*The carbomer used is present in the drops (G2) only at the level of the membrane and therefore in a non-quantifiable manner.

A—Test with Two Surfactants

The behavior of the gelled drops (G2) is studied in the presence of the two surfactants, namely Montanov 68 EC and Simulsol 165.

For this purpose, the four compositions described in the two tables below are prepared:

| Name | INCI name | % w/w |
|---|---|---|
| Osmosis water | Water | Qsp* |
| Microcare PE | Phenoxyethanol | 0.39 |
| Microcare PTG | Pentylenglycol | 0.97 |
| Tego Carbomer 340FD | Carbomer | 0.06 |
| EDETA BD | Disodium EDTA | 0.01 |
| Sodium Hydroxide Pellets PRS codex | Sodium Hydroxide | 0.01 |
| TENSIOACTIF (Montanov 68 EC OU Simulsol 165) | (Cetearyl alcohol & Cetearyl glucoside) OR (PEG 100 Stearate & Glyceryl Stearate) | 2-10 |
| Drops (G2) | Isononyl Isononanoate, CI 61565, CI 60725, coacervate (amodimethicone + carbomer), Dextrin Palmitate | 5.00 |
| Total | | 100.00 |

*qsp: sufficient quantity for with:

| Composition No. | |
|---|---|
| 183 | 2% Montanov 68 EC |
| 184 | 7% Montanov 68 EC |
| 185 | 5% Simulsol 165 |
| 186 | 10% Simulsol 165 |

The drops (G2) were incorporated into these compositions by manual mixing with a spatula for 30 seconds. The stability of the drops (G2) for these formulas 183, 184, 185 and 186 was observed for 1 month at room temperature (RT) and 50° C. The objective of the test at 50° C. is to bring the composition under consideration into accelerated aging conditions.

Results

| Composition | T° C. | VISUAL OBSERVATIONS | TEXTURE of drops (G2) |
|---|---|---|---|
| 183 (2% Montanov 68 EC) | TA | G2 blue, spherical, suspended in the continuous phase | The G2 spread well on the skin. |
| | 50° C. | G2 blue, spherical, smaller than TA, suspended in the more viscous continuous phase. | G2 more resistant (=more viscous gelled oil); spread more with more difficulty. |
| 184 (7% Montanov 68 EC) | TA | G2 blue, spherical, suspended in the continuous phase. | The G2 spread well on the skin. |
| | 50° C. | G2 blue, spherical, smaller than TA, suspended in the more viscous continuous phase. | G2 more resistant (=more viscous gelled oil); spread more with more difficulty. |
| 185 (5% Simulsol 165) | TA | G2 blue, spherical, which cream on the surface of the continuous phase. | The G2 spread well on the skin. |
| | 50° C. | G2 blue-green, spherical, smaller than TA and which cream faster than TA. | G2 harder and some are solid grains difficult to remove. |

| Composition | T° C. | VISUAL OBSERVATIONS | TEXTURE of drops (G2) |
|---|---|---|---|
| 186 (10% Simulsol 165) | TA | G2 blue, spherical, suspended in the continuous phase. | The G2 spread well on the skin. |
| | 50° C. | G2 green-blue, spherical, even smaller than 185 at 50° C. and which cream on the surface of the continuous phase. | G2 harder and some are solid grains difficult to remove. |

In general, it is found that the size of the drops (G2) decreases over time while their viscosity increases when the compositions are maintained at 50° C.

B—Test in Three Rich Creams

In the same manner as in the aforementioned compositions, the above drops (G2) are incorporated at 10% into 3 different rich creams: CNBC-1; CNBC-2; CNBC-3.

Composition of Rich Cream CNBC-1

| Name | INCI name | % w/w |
|---|---|---|
| Osmosis water | Water | qsp |
| Microcare PE | Phenoxyethanol | 0.8 |
| Microcare PTG | Pentylenglycol | 2.0 |
| Keltrol CGT | Xanthan Gum | 0.3 |
| Glycerin | Glycerin | 3.0 |
| Montanov 68 EC | Cetearyl alcohol & Cetearyl glucoside | 8.0 |
| Miglyol 812 N | Caprylic/Capric Triglyceride | 15.0 |
| Lipex Shea | Butyrospermum Parkii (Shea) Butter | 2.0 |
| JAUNE COVARINE W 1793 | CI 11710 (and) Glycerin (and) Aqua (and) Sodium Laureth Sulfate | 0.1 |
| Total | | 100.00 |

* qsp: sufficient quantity for

Composition of Rich Cream CNBC-2

| Name | INCI name | % w/w |
|---|---|---|
| Osmosis water | Water | qsp |
| Microcare PE | Phenoxyethanol | 0.8 |
| Microcare PTG | Pentylenglycol | 2.0 |
| Satiaxane CX 911 | Xanthan Gum | 0.3 |
| Glycerin | Glycerin | 5.0 |
| Simulsol 165 | PEG 100 Stearate & Glyceryl Stearate | 4.0 |
| Lipex 102 | Butyrospermum Parkii (Shea) Butter | 7.0 |
| Lanette 22 | Behenyl alcohol | 2.0 |
| Sweet Almond Oil | Prunus Amygdalus Dulcis (Sweet Almond) Oil | 12.0 |
| ROUGE COVARINE W 3792 | CI 73360 (and) Glycerin (and) Aqua (and) PVP | 0.1 |
| Total | | 100.00 |

* qsp: sufficient quantity for

Composition of Rich Cream CNBC-3

| Name | INCI name | % w/w |
|---|---|---|
| Osmosis water | Water | qsp |
| Microcare PE | Phenoxyethanol | 0.8 |
| Microcare PTG | Pentylenglycol | 2.0 |
| Keltrol CGT | Xanthan Gum | 0.3 |
| Glycerin | Glycerin | 3.0 |
| Montanov 68 EC | Cetearyl alcohol & Cetearyl glucoside | 5.0 |
| Lanette 22 | Behenyl Alcohol | 13.0 |
| Lipex L'sens | Soybean Glycerides (and) Butyrospermum Parkii Butter Unsaponifiables | 2.0 |
| BLEU COVARINE W 6795 | CI 74160 (and) Glycerin (and) Aqua (and) Sodium Laureth Sulfate | 0.1 |
| Total | | 100.00 |

* qsp: sufficient quantity for

The stability of the drops (G2) in these 3 compositions was also studied for 1 month at ambient temperature (RT) and 50° C.

Results

| Sample | T° C. | VISUAL OBSERVATIONS | TEXTURE |
|---|---|---|---|
| CNBC-1 | TA | G2 blue, spherical; Orange cream | Representative of rich cream CNBC-1 |
| | 50° C. | G2 blue, spherical, but with a slight decrease in size; Orange cream | Hardened cream, very consistent with the sample, some solid grains upon application (=G2 harder) |
| CNBC-2 | TA | G2 blue, spherical; Pink cream | Representative of rich cream CNBC-2 |
| | 50° C. | G2 much less blue than TA, spherical, with a decrease in size; Pink cream | All G2 have become small, solid grains). The cream is more fluid on application than TA. |

-continued

| Sample | T° C. | VISUAL OBSERVATIONS | TEXTURE |
|---|---|---|---|
| CNBC-3 | TA | G2 blue, spherical; Bluish cream | Representative of rich cream CNBC-3 |
|  | 50° C. | G2 blue, spherical; Bluish cream tending towards green (yellowing) | The G2 are more noticeable than TA; isolated, the drops (G2) feel more consistent than at TA. |

Again, there is a tendency for drops (G2) to become smaller and stronger at 50° C.

Conclusion

The present study shows that the size of the drops (G2) decreases over time while their viscosity/hardness increases (increase of the local concentration of oily gelling agent) when the latter are in the presence of surfactants or compositions comprising them.

This phenomenon is characterized by a compositional maturation resulting in a migration of a part of the oily phase of the drops (G2) to the surfactants located in the continuous phase of the creams. This has the effect of strongly degrading the organoleptic properties of the composition comprising drops (G2).

Given the stability constraints over time required in the cosmetics field, these results show the impossibility of using drops (G2) in conventional cosmetic compositions (i.e. including surfactants).

Example 2: Preparation of a Composition According to the Invention with Procedure No. 1

A composition according to the invention was prepared by mixing, on the one hand, an emulsion (E1) comprising drops (G1) and, on the other hand, an emulsion (E2) comprising gelled drops (G2).

1. Preparation of the Emulsion (E1)
a. Preparation of a Premix:

Lauroyl Lysine was added to the glycerin with stirring, then the mixture was stirred for 10 minutes and the absence of agglomerates was checked.

b. Preparation of a 10% sodium hydroxide solution:

sodium hydroxide and osmosis water were mixed and then stirred for 10 minutes; and the homogeneity of the solution thus obtained was checked.

c. Preparation of the aqueous phase (OFI):

the osmosis water was then incorporated, followed by phenoxyethanol, and then pentylene glycol and then disodium EDTA;

the carbomer TEGO CARBOMER 340 FD and CARBOPOL ULTREZ 21 POLYMER were sprinkled on the surface;

it was allowed to stand until the total hydration of the carbomers (20-30 minutes) and mixed with stirring using a deflocculator;

it was stirred until the total solubilization of the carbomers (about 30 minutes);

the aforementioned premix (a.) was incorporated then the whole was stirred for 10 minutes;

the above-mentioned sodium hydroxide solution (b.) was added and then the whole was stirred for 10 minutes; and the homogeneity of the solution was verified.

The aqueous phase (OFI) thus obtained comprises the following constituents:

| Name | INCI name | % w/w |
|---|---|---|
| Osmosis water | Water | qsp |
| MICROCARE PE | Phenoxyethanol | 1.2346 |
| MICROCARE EMOLLIENT PTG | Pentyleneglycol | 2.7435 |
| TEGO CARBOMER 340 FD | Carbomer | 0.2333 |
| CARBOPOL ULTREZ 21 POLYMER | Acrylates/C10-30 Alkyl Acrylate Crosspolymer | 0.50 |
| GLYCERINE CODEX | Glycerin | 12.3457 |
| EDETA BD | Disodium EDTA | 0.0412 |
| AMIHOPE ® LL | Lauroyl Lysine | 3.7037 |
| SOLUTION SOUDE à 10% | Sodium Hydroxide | 0.1 |
| Total |  | 100.00 |

* qsp: sufficient quantity for d. Preparation of the oily phase (IFI):

the amodimethicone and the isononyl isononanoate were incorporated, then the whole was gently stirred without incorporating any air bubbles;

the homogeneity of the solution was verified;

the octyldodecanol was incorporated and then stirred for 3 minutes;

PLANTEC REFINED SHEA BUTTER was incorporated;

the mixture thus obtained was heated with stirring to 60° C. for 5 minutes, then the homogeneity of the solution was checked;

a perfume was incorporated and then stirred for 3 minutes;

the homogeneity of the solution was verified.

The oily phase (IFI) thus obtained comprises the following constituents:

| Name | INCI name | % w/w |
|---|---|---|
| ISONONANOATE D'ISONONYLE - DUB ININ | Isononyl Isononanoate | qsp |
| EUTANOL G | Octyldodecanol | 19 |
| PLANTEC REFINED SHEA BUTTER | Butyrospermum Parkii | 19 |
| Perfume | Perfume | 3.33 |
| CAS-3131 | Amodimethicone | 0.2 |
| Total |  | 100.00 | a Preparation of the basic solution (BFI):

sodium hydroxide and osmosis water were mixed and then stirred for 10 minutes; and the homogeneity of the solution thus obtained was checked.

The basic solution (BFI) thus obtained comprises the following constituents:

| Name | INCI name | % w/w |
|---|---|---|
| OSMOSIS WATER | Water | 89.90 |
| SOLUTION MIXED to 10% | Sodium Hydroxide | 10.10 |
| Total | | 100.00 | f. Preparation of the emulsion (E1):

To prepare this emulsion, 10% by weight of oily phase (IFI), 81% of aqueous phase (OFI) and 9% of basic solution (BFI) were used:
- the aqueous phase (OFI) was weighed as described above;
- the oil phase (IFI) was weighed as described above;
- the oil phase and the aqueous phase were then separately placed in a water bath at 60° C. for about 15 minutes, while checking that the temperature of the two phases was the same;
- the aqueous phase was stirred;
- the oil phase is progressively incorporated;
- the stirring speed was gradually increased so as to always have a vortex;
- then stirred for 15 minutes;
- it was then cooled to room temperature with stirring;
- the ethanol was added with stirring;
- after 10 minutes of stirring, the basic solution (BFI) was incorporated and the stirring speed was gradually increased so as to always have a vortex;
- finally, the mixture was stirred for 15 minutes while cooling the mixture with a cold water bath.

The final emulsion (E1) thus obtained comprises the following ingredients:

| AQUEOUS PHASE GEL | | | |
|---|---|---|---|
| Name | INCI name | % w/w phases | % w/w final |
| Osmosis water | Water | qsp | qsp |
| Microcare PE | Phenoxyethanol | 1.11 | 1.00 |
| Microcare PTG | Pentylenglycol | 2.47 | 2.22 |
| Tego Carbomer 340 FD | Carbomer | 0.21 | 0.19 |
| Carbopol Ultrez 21 Polymer | Acrylates/C10-30 Alkyl Acrylate Crosspolymer | 0.45 | 0.405 |
| Glycerine codex (99%) | Glycerin | 11.11 | 10.00 |
| EDETA BD | Disodium EDTA | 0.04 | 0.033 |
| AMIHOPE ® LL | Lauroyl Lysine | 3.33 | 3.00 |
| Denatured ethyl alcohol BITREX/TBA | Ethanol | 5.56 | 5.00 |
| Sodium Hydroxide Pellets PRS codex | Sodium Hydroxide | 0.11 | 0.008 |

2. Preparation of the Emulsion (E2)

a. Preparation of a 10% Sodium Hydroxide Solution:
- sodium hydroxide and osmosis water were mixed and then stirred for 10 minutes; and
- the homogeneity of the solution thus obtained was checked.

b. Preparation of the Aqueous Phase (OF2):
- osmosis water, phenoxyethanol, pentylene glycol, and disodium EDTA were incorporated;
- the carbomer TEGO CARBOMER 340 FD was sprinkled on the surface;
- it was allowed to stand until the total hydration of the carbomer (about 20-30 minutes) and then put together with stirring using a deflocculator;
- it was stirred until complete solubilization of the carbomer (about 30 minutes) and glycerine was incorporated;
- the whole was then stirred for 5 minutes;
- the above-mentioned sodium hydroxide solution (a) was added and then the whole was stirred for 10 minutes; and
- the homogeneity of the solution has been verified.

The aqueous phase (OF2) thus obtained comprises the following constituents:

| Name | INCI name | % w/w |
|---|---|---|
| Osmosis water | Water | qsp |
| Microcare PE | Phenoxyethanol | 0.89 |
| Microcare PTG | Pentylenglycol | 2.22 |
| Tego Carbomer 340 FD | Carbomer | 0.22 |
| Glycerine codex (99%) | Glycerin | 9.00 |
| EDETA BD | Disodium EDTA | 0.036 |
| Sodium Hydroxide Pellets PRS codex | Sodium Hydroxide | 0.033 |
| | | 100.00 | c. Preparation of the Oil Phase (IF2):
- the amodimethicone and the isononyl isononanoate were incorporated and the mixture was gently agitated without incorporating any air bubbles;
- this mixture was heated to 80° C.;
- dextrin palmitate was incorporated while maintaining the temperature;
- it was stirred for 30 minutes;
- the homogeneity of the solution was verified.

The oil phase (IF2) thus obtained comprises the following constituents:

| Name | INCI name | % w/w |
|---|---|---|
| DUB ININ | Isononyl Isononanoate | qsp |
| Rheopearl KL2 | Dextrin Palmitate | 15.00 |
| CAS-3131 | Amodimethicone | 0.20 |
| | | 100.00 | d. Preparation of the Emulsion (E2):

The emulsion (E2) is prepared according to a hot microfluidic process (approximately 80° C.), in particular as described in application FR1558850.

| OF2 | 150 |
|---|---|
| IF2 | 20 |

The final emulsion (E2) thus obtained, comprising monodisperse gelled drops (G2) with a diameter of approximately 800 μm, comprises the following ingredients:

| Name | INCI name | % w/w phases | % w/w Final |
|---|---|---|---|
| AQUEOUS PHASE | | | |
| Osmosis water | Water | 87.5973 | 78.84 |
| Microcare PE | Phenoxyethanol | 0.8889 | 0.80 |

-continued

| Name | INCI name | % w/w phases | % w/w Final |
|---|---|---|---|
| Microcare PTG | Pentylenglycol | 2.2222 | 2.00 |
| Tego Carbomer 340 FD | Carbomer | 0.2222 | 0.20 |
| Glycerine codex (99%) | Glycerin | 9.00 | 8.10 |
| EDETA BD | Disodium EDTA | 0.0360 | 0.03 |
| Sodium Hydroxide Pellets PRS codex | Sodium Hydroxide | 0.0333 | 0.030 |
| | | 100.00 | 90.00 |
| OIL PHASE | | | |
| DUB ININ | Isononyl Isononanoate | 84.80 | 8.48 |
| Rheopearl KL2 | Dextrin Palmitate | 15.00 | 1.50 |
| CAS-3131 | Amodimethicone | 0.20 | 0.02 |
| | | 100.00 | 10.00 |

3. Preparation of the Composition According to the Invention

The composition according to the invention was then obtained by mixing the above-mentioned emulsions (E1) and (E2) as described below.

The emulsion (E2) was filtered using a strainer or sieve whose pore size is smaller than the diameter of the drops (G2) so as to eliminate all or part of the aqueous phase (OF2). The drops (G2) in the colander are then removed to be introduced into the emulsion (E1) with gentle stirring.

Depending on the desired visual aspect and texture, the ratio E1/E2 in mass varies; thus, the drops (G2) may represent between 1% and 20%, or even between 5% and 15%, by weight relative to the total weight of the composition according to the invention.

Example 3: Preparation of a Composition According to the Invention with Procedure No. 2

A procedure for preparing a composition according to the invention described in this example 3 differs from that described in Example 2 in that the gelled drops (G2) are manufactured directly from an emulsion (E1).

1. Preparation of the Emulsion (E1)

This is the emulsion (E1) described in Example 2 above but which differs by:
- the absence of basic solution (BFI), so as to maintain the very fluid nature of this emulsion (E1). Thus, the emulsion (E1) has a viscosity of less than 3000 cPs, as measured at 25° C. according to the measurement protocol relating thereto and described above.
- the addition of CREASPERSE IRON BLUE in the oil phase (IFI) at the end of the preparation protocol of the latter, with homogenization for 5 minutes.

The final emulsion (E1) thus obtained comprises the following ingredients:

| Name | INCI name | % w/w Phases | % w/w final |
|---|---|---|---|
| AQUEOUS PHASE GEL | | | |
| Osmosis water | Water | qsp | qsp |
| Microcare PE | Phenoxyethanol | 1.11 | 1.00 |
| Microcare PTG | Pentylenglycol | 2.47 | 2.222 |
| Teqo Carbomer 340 FD | Carbomer | 0.210 | 0.89 |
| Carbopol Ultrez 21 Polymer | Acrylates/C10-30 Alkyl Acrylate Crosspolymer | 0.45 | 0.405 |
| Glycerine codex (99%) | Glycerin | 11.11 | 10.00 |
| EDETA BD | Disodium EDTA | 0.04 | 0.033 |
| AMIHOPE ® LL | Lauroyl Lysine | 3.33 | 3.00 |
| Denatured ethyl alcohol BITREX/TBA | Ethanol | 5.56 | 5.00 |
| Sodium Hydroxide Pellets PRS codex | Sodium Hydroxide | 0.1 | 0.008 |
| OIL PHASE | | | |
| DUB ININ | Isononyl Isononanoate | 58.47 | 5.847 |
| EUTANOL G | Octyldodecanol | 19.00 | 1.90 |
| PLANTEC REFINED SHEA BUTTER | Butyrospermum Parkii | 19.00 | 1.90 |
| CREASPERSE IRON BLUE | CI 77510 (and) Hydrogenated Polydecene (and) Hydroxystearic Acid | 0.004 | 0.0036 |
| Perfume | Perfume | 3.33 | 0.333 |
| CAS-3131 | Amodimethicone | 0.20 | 0.02 |

2. Preparation of the Composition According to the Invention

The composition according to the invention is prepared according to a hot microfluidic process (approximately 80° C.), in particular as described in the application FR1558850 using the emulsion (E1) above as aqueous phase (OF) and the oil phase (IF2) described below for the formation of drops (G2).

| OIL PHASE (IF2) | | |
|---|---|---|
| DUB ININ | Isononyl Isononanoate | qsp |
| Rheopearl KL2 | Dextrin Palmitate | 15.00 |
| CREASPERSE IRON BLUE | CI 77510 (and) Hydrogenated Polydecene (and) Hydroxystearic Acid | 0.01 |
| CAS-3131 | Amodimethicone | 0.20 |
| TOTAL | | 100.00 |

The composition according to the invention is prepared according to a hot microfluidic process (approximately 80° C.), in particular as described in the application FR1558850.

The flow rates considered (in mL/h) for this reason are the following:

| OF (=emulsion (E1)) | 150 |
|---|---|
| IF2 | 20 |

The manufacture of the drops (G2) is therefore simultaneous with the manufacture of the composition according to the invention. At the end of the manufacture of this composition, a base solution (BFI), identical to that described in Example 2, may be added, preferably microfluidically, so as to enhance the viscosity of the aqueous phase in the composition according to the invention, and thus suspend the drops (G2).

The compositions according to the invention presented in Examples 2 and 3 are particularly advantageous visually and sensorially. Visually, the consumer is faced with compositions comprising drops (G2) visible to the naked eye. On the sensory level, the texture of these compositions is evolutionary. The first moments of application are very aqueous with a marked brittle effect. Then, the feeling evolves towards an oily veil that fades to leave a light and hydrated skin. In parallel, we feel the gelled drops (G2) melt under the effect of spreading which provides an enhanced oily effect.

Example 4: Preparation of a Transparent Composition According to the Invention with Procedure No. 2

The composition of Example 4 differs from that described in Example 3 in that the continuous aqueous phase and the drops (G1) and (G2) are transparent and the oil phase of the drops (G2) is devoid of gelling agent.

1. Preparation of the Emulsion (E1)

| Name | INCI name | % w/w |
|---|---|---|
| Aqueous phase (OFI) | | |
| Osmosis water | Water | qsp |
| MICROCARE PE | PHENOXYETHANOL, AQUA | 0.73 |
| MICROCARE EMOLLIENT PTG | PENTYLENE GLYCOL, AQUA | 1.82 |
| CARBOPOL ETD 2050 POLYMER | CARBOMER | 0.13 |
| GLYCERINE CODEX | GLYCERIN, AQUA | 22.76 |
| ZEMEA PROPANEDIOL | PROPANEDIOL | 13.65 |
| CARBOPOL ULTREZ 30 | Carbomer | 0.13 |
| NIACINAMIDE PC | Niacinamide | 4.55 |
| EDETA BD | DISODIUM EDTA | 0.038 |
| Oil phase (IFI) | | |
| CSF-3100 | Dimethicone | 10.63 |
| Perfume | Fragrance | 0.35 |
| CAS-3131 | Amodimethicone | 0.02 |
| TOTAL | | 100 |

2. Preparation of the Composition According to the Invention

The oil phase (IF2) for drop formation (G2) is described below.

| OIL PHASE (IF2) | | |
|---|---|---|
| DUB ININ | Isononyl Isononanoate | qsp |
| Rheopearl KL2 (optional) | Dextrin palmitate | 0 or 15 |
| CREASPERSE IRON BLUE (optional) | CI 77510 (and) Hydrogenated Polydecene (and) Hydroxystearic Acid | 0 or 0.01 |
| CAS-3131 | Amodimethicone | 0.20 |
| TOTAL | | 100.00 |

Optionally, the oil phase (IF2) may further comprise at least one gelling agent and/or a coloring agent so as to affect the visual aspect of the drop (G2).

When the IF2 is devoid of gelling agent, the procedure for preparing the composition according to Example 4 differs from that described in Example 3 in that it is carried out at room temperature; wherein this procedure may therefore advantageously require the use of an intermediate fluid (FI) comprising only Isononyl Isononanoate, as described in WO2012/120043.

The flow rates considered (in mL/h) are as follows:

| OF (=emulsion (E1) | 150 |
|---|---|
| FI (optional) | 2 |
| IF2 | 20 |

The manufacture of the drops (G2) is therefore simultaneous with the manufacture of the composition according to the invention. At the end of the manufacture of this composition, a base solution (BFI), identical to that described in Example 2, may be added, preferably microfluidically, so as to enhance the viscosity of the aqueous phase in the composition according to the invention, and thus suspend the drops (G2).

Example 5: Example of a Cosmetic Composition

A composition as described in the table below may be prepared according to one of the manufacturing methods described in the present invention and, in particular, according to the method described in Example 3 above.

| Name | INCI name | % w/w final |
|---|---|---|
| AQUEOU PHASE GEL | | |
| Osmosis water | Water | qsp |
| Microcare PE | Phenoxyethanol | 0.1-1% |
| Microcare PTG | Pentylenglycol | 0.5-4% |
| Tego Carbomer 340 FD | Carbomer | 0.01-1% |
| Carbopol Ultrez 21 Polymer | Acrylates/C10-30 Alkyl Acrylate Crosspolymer | 0.1-2% |
| Glycerine codex (99%) | Glycerin | 1-15% |
| EDETA BD | Disodium EDTA | 0.01-0.5% |
| Denatured ethyl alcohol BITREX/TBA | Ethanol | 1-6% |
| Sodium Hydroxide Pellets PRS codex | Sodium Hydroxide | 0.001-0.1% |
| OIL PHASE of the drops (G1) | | |
| DUB ININ | Isononyl Isononanoate | 1-10% |
| | Isostearyl Neopentanoate | 0.5-5% |
| | Isodecyl neopentanoate | 0.5-5% |
| | Isododecane | 0.5-5% |
| PLANTEC REFINED SHEA BUTTER | Butyrospermum Parkii | 0.5-5% |
| | Squalane | 0.1-5% |
| CREASPERSE IRON BLUE | CI 77510 (and) Hydrogenated Polydecene (and) Hydroxystearic Acid | 0-1% |
| Perfume | Perfume | 0.1-1% |
| CAS-3131 | Amodimethicone | 0.01-0.5'''% |
| OIL PHASE of the drops (G2) | | |
| DUB ININ | Isononyl Isononanoate | 0.1-5% |
| | Isostearyl Neopentanoate | 0.5-5% |
| | Octyldodecyl myristate | 0.5-5% |
| | Neopentyl glycol diheptanoate and isododecane | 0.5-5% |
| Rheopearl KL2 | Dextrin Palmitate | 0.5-5% |
| CREASPERSE IRON BLUE | CI 77510 (and) Hydrogenated Polydecene (and) Hydroxystearic Acid | 0-1% |
| CAS-3131 | Amodimethicone | 0.01-0.5% |
| TOTAL | | 100.00 |

A composition according to Example 5 may be applied every morning on the face to moisturize, strengthen the barrier function, protect and bring radiance to the skin.

It has been observed that a composition according to Example 5, in use, especially as indicated above, allows prolonged microdiffusion of the active ingredients, in particular moisturizing and anti-aging agents, and in fact provides a continuous action in the heart of the skin.

The invention claimed is:

1. A composition in the form of an oil-in-water emulsion, comprising a continuous aqueous phase and a dispersed oil phase in the form of drops (G1) and (G2),
    wherein the drops (G1) comprise an oil phase and a shell formed of at least one anionic polymer (PA1) and at least one cationic polymer (PC1), wherein the size of the drops (G1) is less than 500 µm,
    wherein the drops (G2) comprise an oil phase and a shell, said shell being formed of at least one anionic polymer (PA2), identical to or different from (PA1), and at least one cationic polymer (PC2), identical or different from (PC1), wherein the size of the drops (G2) is greater than 500 µm,
    wherein the drops (G1) and (G2) are different in nature, in regard to the nature of the anionic and cationic polymers, or oils and/or additional compounds and/or active agents
    wherein the anionic polymers (PA1) and (PA2) are hydrophilic, and the cationic polymers (PC1) and (PC2) are liposoluble, and
    wherein the composition does not include a surfactant.

2. The composition according to claim 1, wherein the oil phase of the drops (G2) comprises at least one gelling agent.

3. The composition according to claim 1, wherein the oil phase of the drops (G1) and/or drops (G2) comprises at least one oil (H1) selected from the group consisting of hydrocarbon-based oils of animal origin, synthetic esters and ethers, linear or branched hydrocarbons of mineral or synthetic origin, silicone oils, fatty alcohols having from 8 to 26 carbon atoms, fluorinated oils partially hydrocarbonated and/or siliconated and their mixtures.

4. The composition according to claim 1, wherein the anionic polymers (PA1) and (PA2), which are identical or different, are polymers comprising monomeric units comprising at least one carboxylic acid function.

5. The composition according to claim 1, wherein the composition comprises from 0.01% to 10% by weight of anionic polymer(s) (PA1) and (PA2), relative to the total weight of the composition.

6. The composition according to claim 1, wherein the cationic polymers (PC1) and (PC2), identical or different, have the following formula:

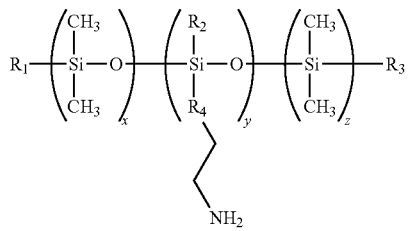

in which:
R₁, R₂ and R₃, independently of each other, represent OH or CH₃;
R₄ represents a —CH₂—group or a —X—NH—group in which X is a divalent alkylene radical with C3 or C4;
x is an integer from 10 to 5000;
y is an integer between 2 and 1000; and
z is an integer between 0 and 10.

7. The composition according to claim 1, wherein the drops (G1) and (G2) comprise from 0.01% to 10% by weight of cationic polymer(s) (PC1) and (PC2), relative to the total weight of the oil phase of the drops (G1) and (G2).

8. The composition according to claim 2, wherein the drop gelling agent (G2) is selected from the group consisting of organic, inorganic, polymeric or molecular lipophilic gelling agents; fatty substances that are solid at room temperature and pressure; and their mixtures.

9. The composition according to claim 8 wherein the gelling agent is selected from the group consisting of polyacrylates, dextrin and fatty acid esters, esters of glycerol and fatty acid(s), polyamides, and mixtures thereof.

10. The composition according to claim 9, wherein the dextrin and fatty acid esters are selected from the group consisting of dextrin palmitates, dextrin myristates, dextrin palmitates/ethylhexanoates, and mixtures thereof.

11. The composition according to claim 8, wherein the gelling agent is selected from the group consisting of modified clays, silicas and mixtures thereof.

12. The composition according to claim 1, wherein the composition comprises a weight ratio "drops (G1)/drops (G2)" of between 0.03 and 50.

13. The composition according to claim 1, further comprising at least one active agent selected from hydrating agents, healing agents, depigmenting agents, UV filters, desquamating agents, antioxidants, agents stimulating the synthesis of dermal and/or epidermal macromolecular agents, contracting agents, antiperspirants, soothing agents, anti-aging agents, perfuming agents and mixtures thereof.

14. The composition according to claim 1, characterized in that the drops (G1) and/or (G2) further comprise at least one coloring agent.

15. The composition according to claim 1, wherein the composition comprises more than 10% by weight of oil phase relative to the total weight of the composition.

16. A composition in the form of an oil-in-water emulsion, comprising a continuous aqueous phase and a dispersed oil phase in the form of drops (G1) and (G2),
    wherein the drops (G1) comprise an oil phase and a shell formed of at least one anionic polymer (PA1) and at least one cationic polymer (PC1), wherein the size of the drops (G1) is less than 500 µm,
    wherein the drops (G2) comprise an oil phase and a shell, said shell being formed of at least one anionic polymer (PA2), identical to or different from (PA1), and at least one cationic polymer (PC2), identical or different from (PC1), wherein the size of the drops (G2) is greater than 500 µm, and
    wherein the drops (G1) and (G2) are different in nature, in regard to the nature of the anionic and cationic polymers, or oils and/or additional compounds and/or active agents,
    wherein the anionic polymers (PA1) and (PA2) are hydrophilic, and the cationic polymers (PC1) and (PC2) are lipophilic or liposoluble,
    wherein the anionic polymer (PA1) is selected from the group consisting of carbomers and copolymers of acrylic acid or maleic acid and other monomers, said other monomers being selected from the group consisting of: acrylamide, alkyl acrylates, C₅-C₈ alkyl acrylates, C₁₀-C₃₀ alkyl acrylates, C₁₂-C₂₂ alkyl methacrylates, methoxy-polyethylene glycol methacrylates, hydroxyester acrylates, crosspolymer acrylates, and mixtures thereof, and
    the composition does not include a surfactant.

17. The composition of claim 16, wherein the anionic polymer (PA1) is selected from the group consisting of carbomers and crosslinked acrylates/$C_{10-30}$ alkyl acrylate copolymers.

18. The composition of claim 16, wherein the anionic polymer (PA1) is a carbomer.

19. The composition of claim 1, wherein at least one of the cationic polymers (PC1) and (PC2) is amodimethicone.

20. The composition of claim 16, wherein at least one of the cationic polymers (PC1) and (PC2) is amodimethicone.

* * * * *